(12) United States Patent
Black et al.

(10) Patent No.: US 10,172,655 B2
(45) Date of Patent: Jan. 8, 2019

(54) OSTEOSYNTHESIS SYSTEM, ASSEMBLIES AND COMPONENTS

(71) Applicant: Degen Medical, Inc., Florence, SC (US)

(72) Inventors: Craig Black, Florence, SC (US); Willie S. Edwards, Jr., Florence, SC (US); Rakesh P. Chokshi, Florence, SC (US)

(73) Assignee: DeGen Medical, Inc., Florence, SC (US)

( * ) Notice: Subject to any disclaimer, the term of this patent is extended or adjusted under 35 U.S.C. 154(b) by 947 days.

(21) Appl. No.: 14/502,721

(22) Filed: Sep. 30, 2014

(65) Prior Publication Data

US 2015/0094772 A1   Apr. 2, 2015

Related U.S. Application Data

(60) Provisional application No. 61/885,105, filed on Oct. 1, 2013.

(51) Int. Cl.
  *A61B 17/80* (2006.01)

(52) U.S. Cl.
  CPC ...... *A61B 17/8052* (2013.01); *A61B 17/8033* (2013.01); *A61B 17/8042* (2013.01)

(58) Field of Classification Search
  CPC ............ A61B 17/8033; A61B 17/8042; A61B 17/8052; A61B 17/80; A61B 17/8004; A61B 17/8061
  USPC .............................. 606/70–71, 280–299, 905
  See application file for complete search history.

(56) References Cited

U.S. PATENT DOCUMENTS

| | | | |
|---|---|---|---|
| 4,503,848 A | 3/1985 | Caspar et al. |
| 5,549,612 A | 8/1996 | Yapp et al. |
| 5,616,144 A | 4/1997 | Yapp et al. |
| 6,139,550 A | 10/2000 | Michelson |
| 6,193,721 B1 | 2/2001 | Michelson |
| 6,306,139 B1 | 10/2001 | Fuentes |
| 6,383,186 B1 | 5/2002 | Michelson |
| 6,398,783 B1 | 6/2002 | Michelson |
| 6,416,528 B1 | 7/2002 | Michelson |

(Continued)

OTHER PUBLICATIONS

International Bureau of WIPO, "International Preliminary Report on Patentability", for Intl. App. No. PCT/US2014/058418, dated Apr. 5, 2016, pp. 1-11.

(Continued)

*Primary Examiner* — Zade Coley
*Assistant Examiner* — Jessica Weiss
(74) *Attorney, Agent, or Firm* — Buchanan Van Tuinen LLC

(57) ABSTRACT

Osteosynthesis systems useful in the fusion of cervical vertebrae are described. An osteosynthesis system includes a plate, a set of anchors, a set of locking members, and a set of pins. The plate defines anchor passageways that receive the anchors, locking member passageways that receive the locking member passageways; and pin passageways that receive the pins. Each of the locking member passageways partially intersects one of the anchor passageways and each of the pin passageways provides a passageway extending from a side of the plate to one of the locking member passageways. Each of the locking members is rotatable within the respective one of the locking member passageways and is adapted to engage an adjacent anchor from the side.

18 Claims, 15 Drawing Sheets

(56) References Cited

U.S. PATENT DOCUMENTS

| | | |
|---|---|---|
| 6,428,542 B1 | 8/2002 | Michelson |
| 6,454,771 B1 | 9/2002 | Michelson |
| 6,527,776 B1 | 3/2003 | Michelson |
| 6,592,586 B1 | 7/2003 | Michelson |
| 6,616,666 B1 | 9/2003 | Michelson |
| 6,620,163 B1 | 9/2003 | Michelson |
| 6,712,818 B1 | 3/2004 | Michelson |
| 6,916,320 B2 | 7/2005 | Michelson |
| 6,926,718 B1 | 8/2005 | Michelson |
| 6,936,050 B2 | 8/2005 | Michelson |
| 6,936,051 B2 | 8/2005 | Michelson |
| 6,969,390 B2 | 11/2005 | Michelson |
| 7,074,221 B2 | 7/2006 | Michelson |
| 7,077,844 B2 | 7/2006 | Michelson |
| 7,097,645 B2 | 8/2006 | Michelson |
| 7,137,984 B2 | 11/2006 | Michelson |
| 7,306,605 B2 | 12/2007 | Ross |
| 7,452,370 B2 | 11/2008 | Anderson |
| 7,625,381 B2 | 12/2009 | Michelson |
| 7,651,497 B2 | 1/2010 | Michelson |
| 7,704,255 B2 | 4/2010 | Michelson |
| 7,727,266 B2 | 6/2010 | Lindemann et al. |
| 7,811,285 B2 | 10/2010 | Michelson |
| 7,875,061 B2 | 1/2011 | Bolger et al. |
| 7,985,224 B2 | 7/2011 | Michelson |
| 8,043,346 B2 | 10/2011 | Markworth |
| 8,048,075 B2 | 11/2011 | Michelson |
| 8,070,749 B2 | 12/2011 | Stern |
| 8,123,788 B2 | 2/2012 | Michelson |
| 8,172,842 B2 * | 5/2012 | Sasing ............... A61B 17/1655 606/71 |
| 8,262,708 B2 | 9/2012 | Michelson |
| 8,454,667 B2 | 6/2013 | Humphreys |
| 8,480,717 B2 | 7/2013 | Michelson |
| 8,556,895 B2 | 10/2013 | Stern |
| 8,858,556 B2 | 10/2014 | Stern |
| 9,370,386 B2 * | 6/2016 | Galm ................... A61B 17/808 |
| 9,526,628 B2 * | 12/2016 | Krueger ................. A61F 2/442 |
| 9,662,145 B2 * | 5/2017 | Harris ............... A61B 17/7059 |
| 2002/0045896 A1 | 4/2002 | Michelson |
| 2002/0128655 A1 | 9/2002 | Michelson |
| 2002/0183757 A1 | 12/2002 | Michelson |
| 2003/0018335 A1 | 1/2003 | Michelson |
| 2003/0045880 A1 | 3/2003 | Michelson |
| 2003/0181912 A1 | 9/2003 | Michelson |
| 2003/0191471 A1 | 10/2003 | Michelson |
| 2003/0191472 A1 | 10/2003 | Michelson |
| 2004/0122426 A1 | 6/2004 | Michelson |
| 2004/0220572 A1 | 11/2004 | Michelson |
| 2004/0236334 A1 | 11/2004 | Michelson |
| 2004/0236335 A1 | 11/2004 | Michelson |
| 2005/0038436 A1 | 2/2005 | Michelson |
| 2005/0059971 A1 | 3/2005 | Michelson |
| 2005/0075633 A1 * | 4/2005 | Ross ................... A61B 17/7059 606/280 |
| 2005/0187552 A1 | 8/2005 | Michelson |
| 2006/0247639 A1 | 11/2006 | Anderson |
| 2006/0293669 A1 * | 12/2006 | Lindemann ........ A61B 17/7059 606/86 A |
| 2007/0123881 A1 * | 5/2007 | Ralph ................ A61B 17/8023 606/281 |
| 2008/0027439 A1 * | 1/2008 | Sasing ............... A61B 17/1655 606/279 |
| 2008/0287999 A1 | 11/2008 | Markworth |
| 2008/0306550 A1 * | 12/2008 | Matityahu .......... A61B 17/1728 606/290 |
| 2010/0145459 A1 | 6/2010 | McDonough et al. |
| 2012/0095513 A1 * | 4/2012 | Humphreys ....... A61B 17/8033 606/289 |
| 2012/0158058 A1 | 6/2012 | Michelson |
| 2012/0158068 A1 * | 6/2012 | Humphreys ....... A61B 17/8042 606/286 |
| 2013/0006309 A1 | 1/2013 | Lorio et al. |
| 2013/0013002 A1 | 1/2013 | Michelson |
| 2013/0197588 A1 * | 8/2013 | Abdou ............... A61B 17/8042 606/279 |
| 2013/0204300 A1 | 8/2013 | Michelson |
| 2014/0371798 A1 * | 12/2014 | Platt ...................... A61B 17/80 606/281 |

OTHER PUBLICATIONS

International Searching Authority, International Search Report and Written Opinion for International Application No. PCT/US2014/058418, dated Mar. 10, 2015, pp. 1-15.

* cited by examiner

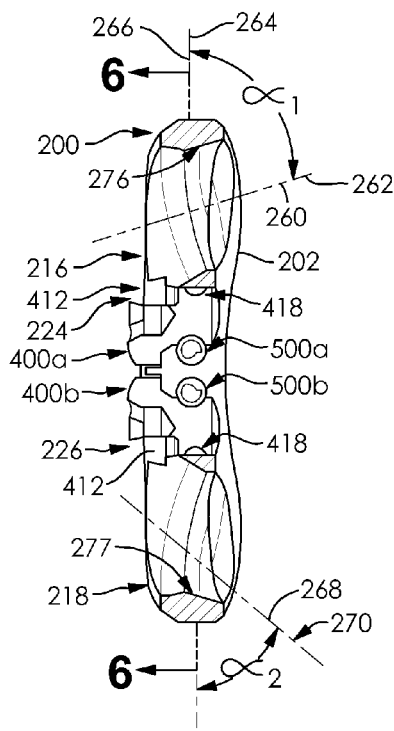
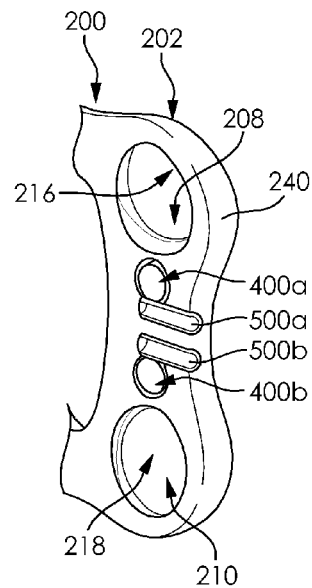
FIG. 5
FIG. 6
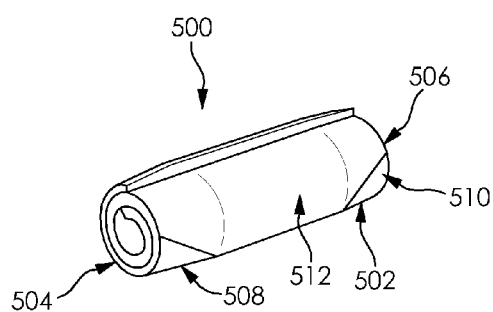
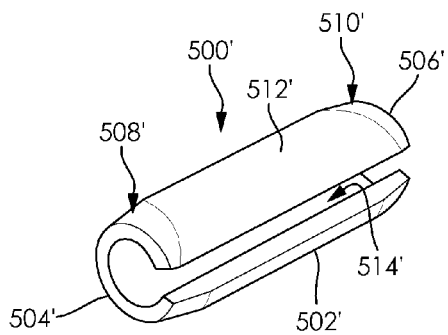
FIG. 7A
FIG. 7B

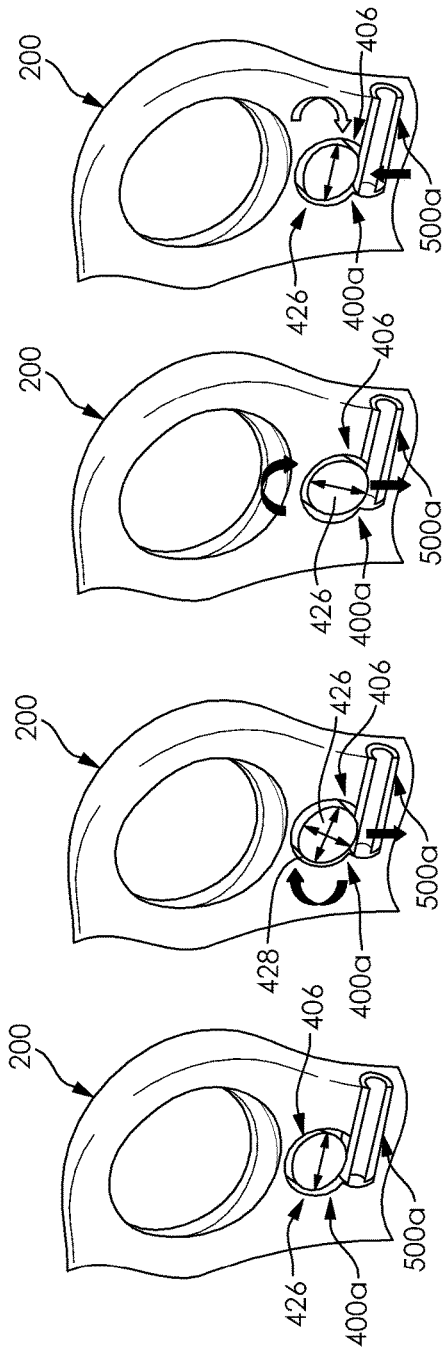
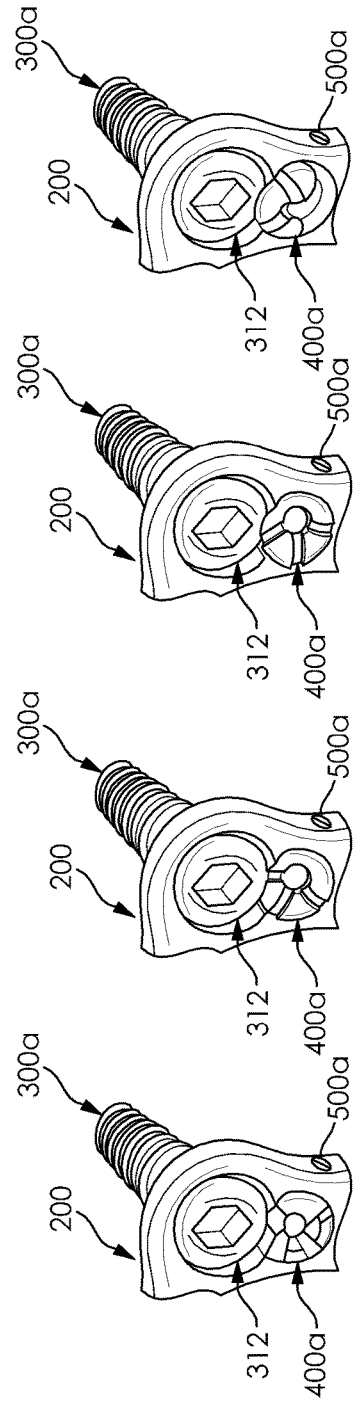

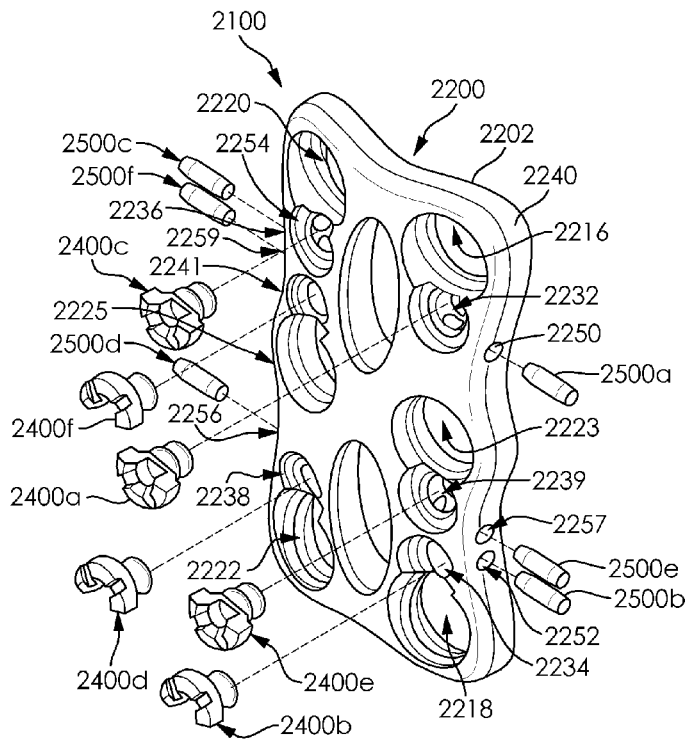
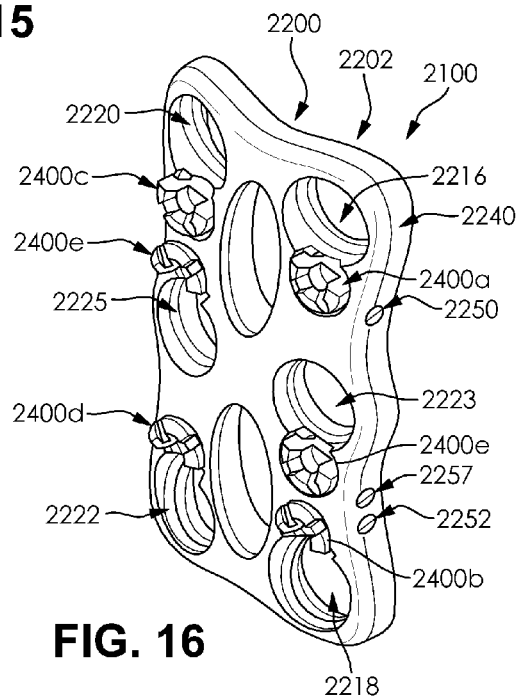
FIG. 15
FIG. 16

OSTEOSYNTHESIS SYSTEM, ASSEMBLIES AND COMPONENTS

RELATED APPLICATION

This application claims the benefit of U.S. Provisional Application No. 61/885,105 filed on Oct. 1, 2013. The disclosure of this related application is hereby incorporated into this disclosure in its entirety.

FIELD

The disclosure relates to the technical field of osteosynthesis systems useful for connecting bones or portions of bones to each other in an animal, such as a human.

BACKGROUND

The art includes several examples of osteosynthesis systems, assemblies and components useful for connecting bones or portions of bones to each other. Several designs, for example, include plates that span the bones or portions of bones to be connected, and anchors that secure the plates to the bones or portions of bones. In one example, described in U.S. Pat. No. 8,454,667, a plate includes a hole extending between surfaces of the plate. A spring-loaded retaining element partially overlaps the hole to help prevent inadvertent backing out of a fastener disposed in the hole and bone. In another example, described in U.S. Pat. No. 7,727,266, a deflectable ring is included to prevent backing out of a fastener.

Despite these and other example, a need exists for improved osteosynthesis systems, assemblies and components.

BRIEF SUMMARY OF EXAMPLES

Various example osteosynthesis systems useful for connecting bones or portions of bones to each other in an animal such as a human are described and illustrated herein.

An example osteosynthesis system comprises a plate having a main body having a side and defining a set of anchor passageways, a set of locking member passageways, and a set of pin passageways, each of the locking member passageways partially intersecting one of the anchor passageways and each of the pin passageways providing a passageway extending from the side of the main body to one of the locking member passageways; a set of anchors, each anchor disposed in one of the anchor passageways and defining a proximal surface, a distal end, and a circumferential shoulder located distal to the proximal surface; a set of locking members, each locking member defining a circumferential groove disposed in one of the locking member passageways and rotatable within the one of the locking member passageways to engage the circumferential shoulder of the anchor disposed in the anchor passageway partially intersected by the one of the locking member passageways; and a set of pins, each pin disposed in one of the pin passageways and partially disposed within the circumferential groove defined by the locking member disposed in the locking member passageway in communication with the pin passageway.

Another example osteosynthesis system comprises a plate defining a series of anchor passageways, a set of anchors individually disposable within the anchor passageways, at least one locking member configured to engage only a single anchor of the set of anchors to retain the single anchor of the set of anchors within an anchor passageway, and at least one locking member configured to engage more than one anchor of the set of anchors to retain each of the more than one anchor of the set of anchors within an anchor passageway.

Another example osteosynthesis system comprises a plate defining a main body, a side, a first series of anchor passageways, a second set of anchor passageways, a set of anchors, each anchor of the set of anchors individually disposable within an anchor passageway of the first and second series of anchor passageways, and a set of locking members, each locking member of the set of locking members defining a circumferential groove and configured to engage at least one anchor of the set of anchors to retain the at least one anchor within an anchor passageway of one of the first and second series of anchor passageways; wherein each anchor passageway of the first series of anchor passageways allows an anchor of the set of anchors to be disposed at a hyperangulation angle; and wherein each anchor passageway of the second series of anchor passageways does not allow an anchor of the set of anchors to be disposed at a hyperangulation angle.

Additional understanding of the osteosynthesis systems can be obtained with review of the detailed description, below, and the appended drawings.

DESCRIPTION OF FIGURES

FIG. 5 is a sectional view of the plate assembly of the osteosynthesis system illustrated in FIG. 1, taken along line 5-5 in FIG. 2.

FIG. 6 is a sectional view of the plate assembly of the osteosynthesis system illustrated in FIG. 1., taken along line 6-6 in FIG. 5.

FIG. 7A is a magnified view of one pin of the osteosynthesis system illustrated in FIG. 1.

FIG. 7B is a magnified view of an alternative pin.

FIG. 10A is a magnified partial sectional view of the plate assembly of the osteosynthesis system illustrated in FIG. 1. The locking member and pin are shown in a first configuration.

FIG. 10B is a magnified partial sectional view of the plate assembly of the osteosynthesis system illustrated in FIG. 1. The locking member and pin are shown in a second configuration.

FIG. 10C is a magnified partial sectional view of the plate assembly of the osteosynthesis system illustrated in FIG. 1. The locking member and pin are shown in a third configuration.

FIG. 10D is a magnified partial sectional view of the plate assembly of the osteosynthesis system illustrated in FIG. 1. The locking member and pin are shown in a fourth configuration.

FIG. 10E is a partial perspective view of the plate assembly of the osteosynthesis system illustrated in FIG. 1. The locking member is shown in the first configuration illustrated in FIG. 10A.

FIG. 10F is a partial perspective view of the plate assembly of the osteosynthesis system illustrated in FIG. 1. The locking member is shown in the second configuration illustrated in FIG. 10B.

FIG. 10G is a partial perspective view of the plate assembly of the osteosynthesis system illustrated in FIG. 1. The locking member is shown in the third configuration illustrated in FIG. 10C.

FIG. 10H is a partial perspective view of the plate assembly of the osteosynthesis system illustrated in FIG. 1. The locking member is shown in the fourth configuration illustrated in FIG. 10D.

FIG. 15 is an exploded view of another osteosynthesis system.

FIG. 16 is a perspective view of the plate assembly of the osteosynthesis system illustrated in FIG. 15.

DESCRIPTION OF EMBODIMENTS

The following detailed description and the appended drawings describe and illustrate various example embodiments. The description and illustration of these examples are provided to enable one skilled in the art to make and use an osteosynthesis system and related assemblies and components. They are not intended to limit the scope of the claims in any manner.

As used herein, the term "engage" and grammatically related terms means to make contact with a structure.

Figure 9A:
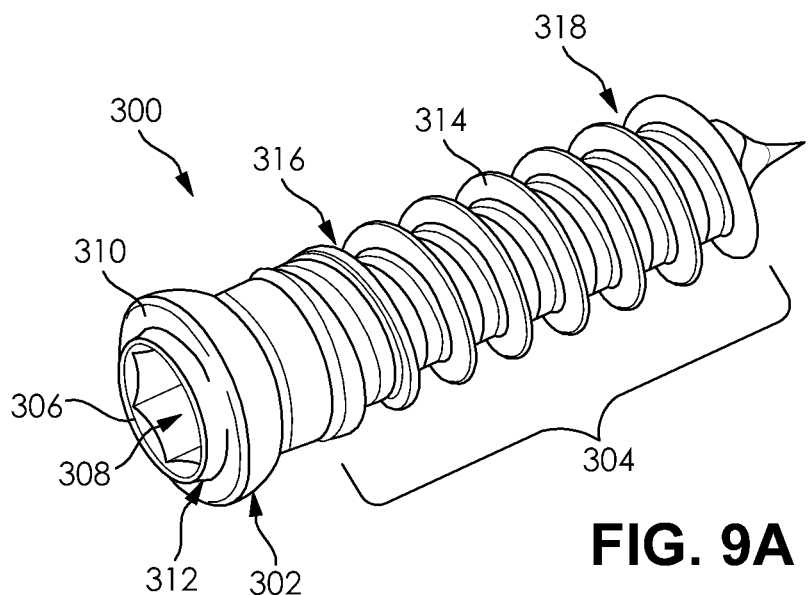
FIG. 9A is a perspective view of one anchor of the osteosynthesis system illustrated in FIG. 1.

In the drawings and the description, a reference number followed by a lower case letter, e.g., 300a, refers to a specific structure that is a member of a group of related structures that are denoted by the same reference number but with a different letter, e.g., 300b. For these structures, use of the reference number in the drawings and/or description without a letter, e.g., refers to a generic representation of the specific structures referenced by the various number/letter combinations. For example, in FIG. 1, the specific anchors are indicated by reference numbers 300a, 300b, 300c, and 300d. In FIG. 9A, though, reference number 300 indicates a generic representation of an anchor used in the osteosynthesis system 100 illustrated in FIG. 1.

Figure 1:
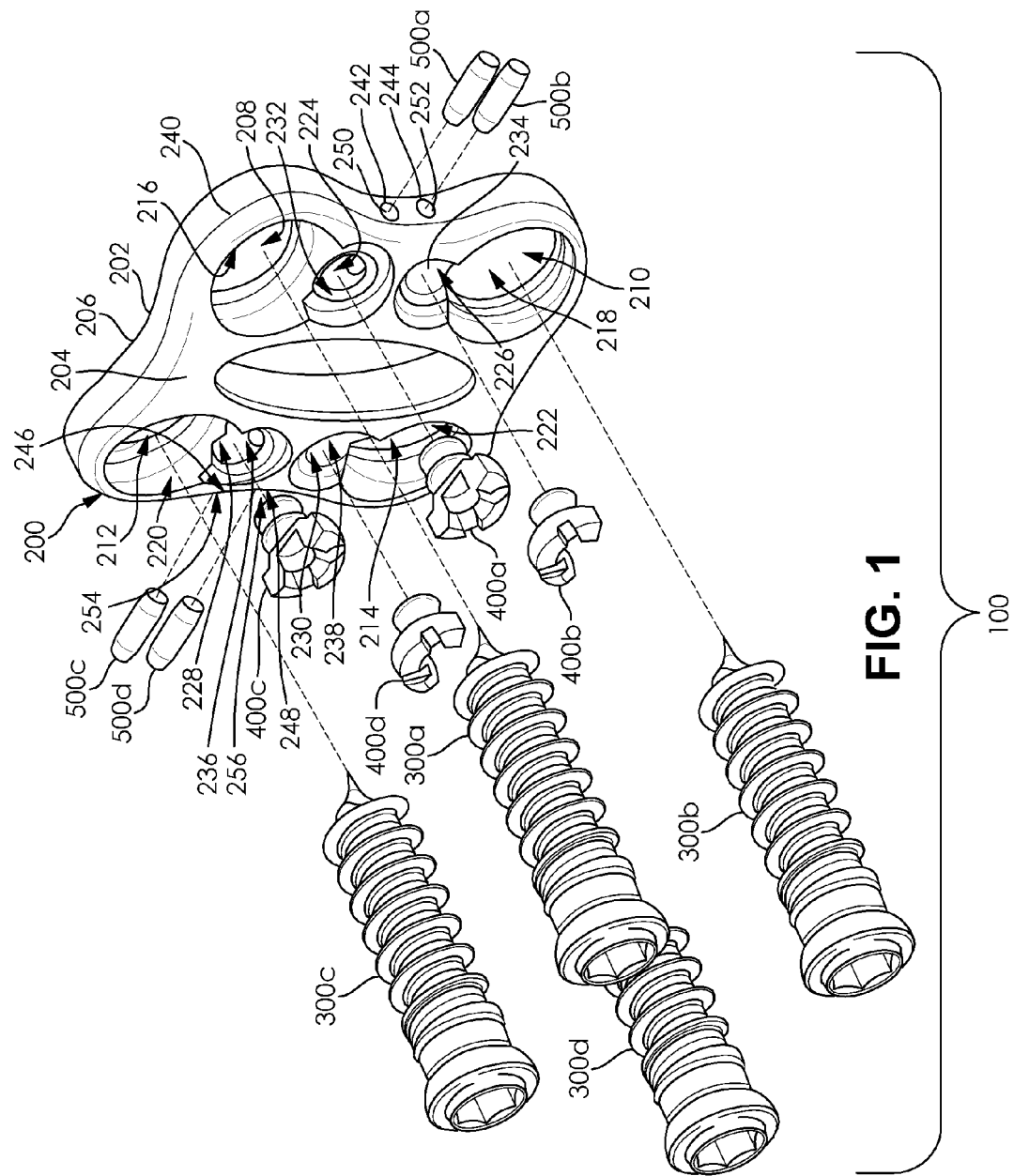
FIG. 1 is an exploded view of an osteosynthesis system.
Figure 2:
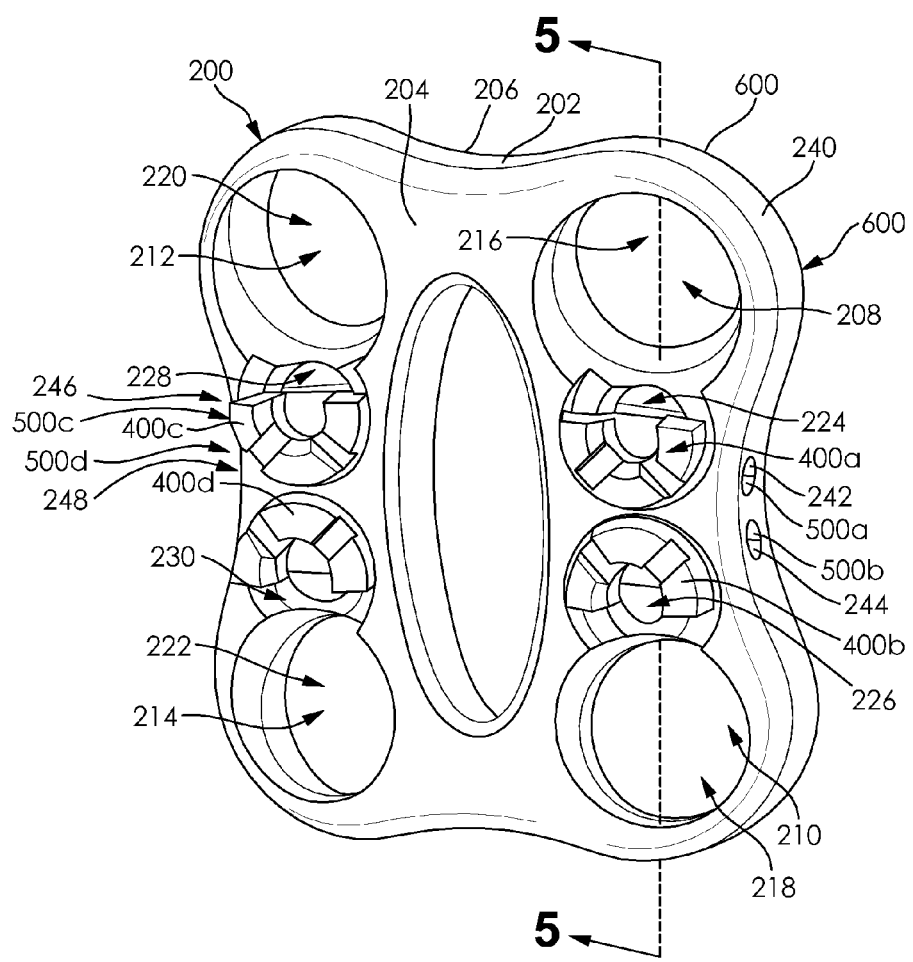
FIG. 2 is a perspective view of the plate assembly of the osteosynthesis system illustrated in FIG. 1.
Figure 3:
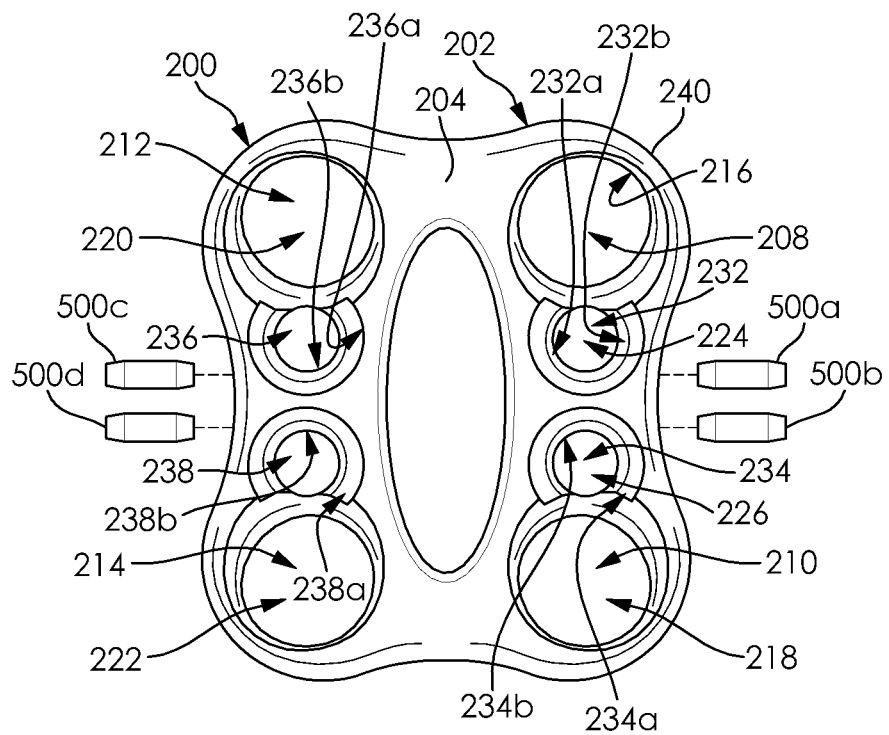
FIG. 3 is a top view of the plate and pins of the osteosynthesis system illustrated in FIG. 1.
Figure 4:
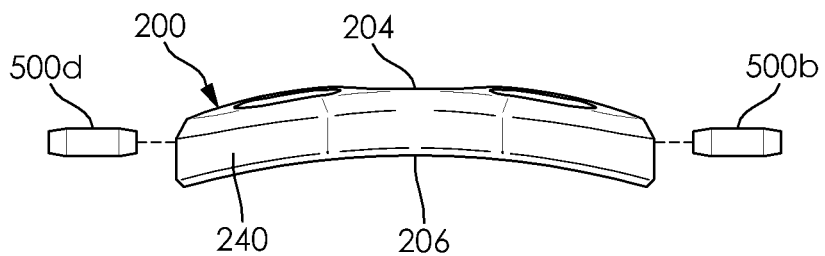
FIG. 4 is an end view of the plate and pins illustrated in FIG. 3.

Each of FIGS. 1, 2, 3, 4, 5, 5A, 6, 7A, 8, and 9A illustrates an osteosynthesis system 100 or a component of the osteosynthesis system 100. FIG. 2 illustrates a plate assembly 600 of the osteosynthesis system 100. Each of FIGS. 7B and 9B illustrate alternative components of the osteosynthesis system 100. Each of FIGS. 10A, 10B, 10C, 10D, 10E, 10F, 10G, and 10H illustrate a portion of the osteosynthesis system 100 in a configuration achievable during use of the osteosynthesis system 100.

As an overview, with reference to FIG. 1, the osteosynthesis system 100 includes a plate 200, a set of anchors 300a, 300b, 300c, 300d, a set of locking members 400a, 400d, 400c, 400d, and a set of pins 500a, 500b, 500c, 500d. The plate 200 defines three sets of passageways: anchor passageways 216, 218, 220, 222; locking member passageways 232, 234, 236, 238; and pin passageways 250, 252, 254, 256. Each of the locking member passageways 232, 234, 236, 238 partially intersects one of the anchor passageways 216, 218, 220, 222. Each of the pin passageways 250, 252, 254, 256 provides a passageway extending from the side 240 of the main body 202 of the plate 200 to one of the locking member passageways 232, 234, 236, 238. Each of the anchors 300a, 300b, 300c, 300d is disposed in one of the anchor passageways 216, 218, 220, 222. Each of the locking members 400a, 400b, 400c, 400d is disposed in one of the locking member passageways 232, 234, 236, 238 and is rotatable within the respective one of the locking member passageways 232, 234, 236, 238. Each of the pins 500a, 500b, 500c, 500d is disposed in one of the pin passageways 250, 252, 254, 256.

In use, and as described in greater detail below, one of the locking members 400a, 400d, 400c, 400d is rotated within its respective one of the locking member passageways 232, 234, 236, 238 until it engages the respective one of the anchors 300a, 300b, 300c, 300d disposed in the respective one of the anchor passageways 216, 218, 220, 222 that intersects the one of the locking member passageways 232, 234, 236, 238 within which the one of the locking members 400a, 400d, 400c, 400d is disposed. One of the pins 500a, 500b, 500c, 500d that is disposed in the one of the pin passageways 250, 252, 254, 256 that is in communication with the one of the locking member passageways 232, 234, 236, 238 within which the one of the locking members 400a, 400d, 400c, 400d is disposed engages the one of the locking members 400a, 400d, 400c, 400d during its rotation within the one of the locking member passageways 232, 234, 236, 238 in a manner that provides one or more stop positions for the one of the locking members 400a, 400d, 400c, 400d, including a stop position in which the one of the locking members 400a, 400d, 400c, 400d is engaged with the respective one of the anchors 300a, 300b, 300c, 300d. This secures the respective one of the anchors 300a, 300b, 300c, 300d in its respective anchor passageway 216, 218, 220, 222. This can be repeated for each of the locking members 400a, 400d, 400c, 400d.

As best illustrated in FIG. 1, osteosynthesis system 100 includes plate 200 having a main body 202 with opposing first 204 and second 206 sides. The main body 202 defines anchor openings 208, 210, 212 and 214 that extend through the main body 202. Each of the anchor openings 208, 210, 212, 214 defines an anchor passageway, represented by the reference number of the respective anchor opening increased by 8, that extends between the first 204 and second 206 sides. Thus, the main body 202 has four anchor passageways 216, 218, 220, and 222.

Each of the anchor passageways 216, 218, 220, 222 has a central axis that lies on a plane that is disposed at an angle to a plane that contains a central longitudinal axis of the main body 202. For example, as best illustrated in FIG. 5, anchor passageway 216 has central axis 260 that lies on plane 262, which is disposed at angle $\alpha_1$ to plane 264, which contains central longitudinal axis 266 of the main body 202 of the plate 200. Similarly, anchor passageway 218 has central axis 268 that lies on plane 270, which is disposed at angle $\alpha_2$ to plane 264. This configuration places anchors disposed within the anchor passageways 216, 218, 220, 222 at an angle to the plane 264 that contains central longitudinal axis 266 of the main body 202 of the plate 200. The anchor passageways 216, 218, 220, 222 can be disposed at any suitable angle, and a skilled artisan will be able to select appropriate angles for an osteosynthesis system according to a particular embodiment based on various considerations, including the intended use and location at which the particular osteosynthesis system will be implanted. As best illustrated in FIG. 1 and FIG. 5, it is considered advantageous to have the anchor passageways on one end of the plate, such as anchor passageways 216 and 220, to have axes disposed on the same plane 262 and, as a result, at the same angle $\alpha_1$ to the plane 264 containing the central longitudinal axis 266 of the main body 202. Similarly, it is considered advantageous to have the anchor passageways on the other end of the plate, such as anchor passageways 218 and 222, to have axes disposed on the same plane 270 and, as a result, at the same angle $\alpha_2$ to the plane 264 containing the central longitudinal axis 266 of the main body 202. Also, as best illustrated in FIG. 5, it is considered advantageous to configure the anchor passageways 216, 218, 220, 222 such that angles $\alpha_1$, $\alpha_2$ are inverses of each other relative to the plane 264 containing the central longitudinal axis 266 of the main body 202. For example, angle $\alpha_1$ can be about 30° and angle $\alpha_2$ can be about −30°. It is noted, though, that different angles can be used and, indeed, each of the anchor passageways in an osteosynthesis system according to a particular embodiment can be disposed at an angle that is different from one, more than one, or all of the anchor passageways defined by the plate of the particular osteosynthesis system. Also, as described in greater detail below, the locking members 400a, 400d, 400c, 400d define structure that facilitate the achievement of hyperangulation of the anchors 300a, 300b, 300c, 300d within the anchor passageways 216, 218, 220, 222.

Figure 5A:
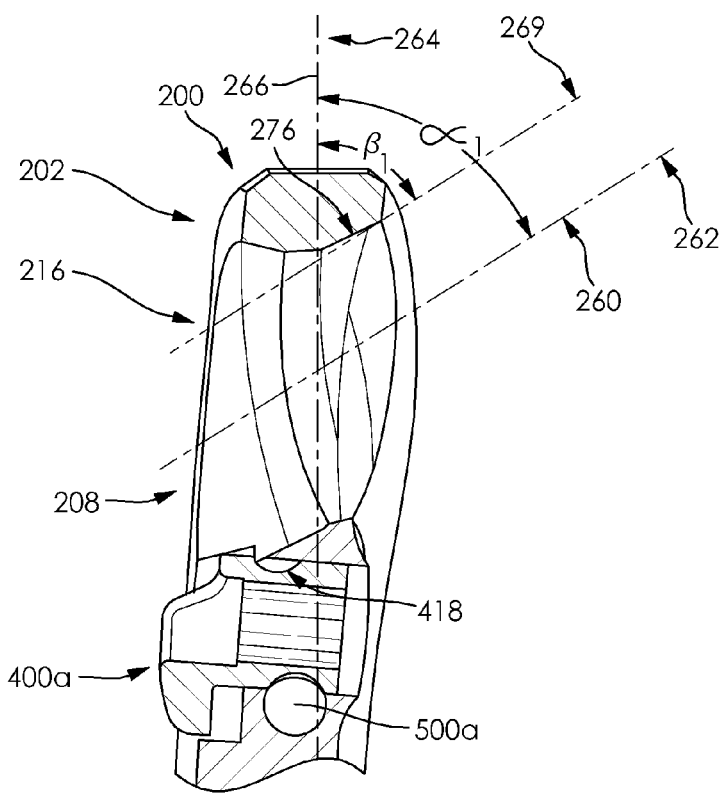
FIG. 5A is a partial magnified view of the plate assembly illustrated in FIG. 5.

Each of the anchor passageways 216, 218, 220, 222, also define ramps 276, 277, and others not illustrated in the Figures, as well. Each ramp 276, 277, and others not illustrated in the Figures, may have any suitable cross-sectional shape and size. The ramps 276, 277, and others not illustrated in the Figures, help to facilitate the achievement of hyperangulation of an anchor 300a, 300b, 300c, 300d. As best illustrated in FIG. 5A, for example, the anchor passageway 216 defines a ramp 276 having a ramp angle $\beta_1$ that is disposed at an angle with respect to the plane 264 on which the central longitudinal axis 266 of the main body 202 of the plate 200 lies. The ramp angle $\beta_1$ lies on a ramp plane 269 and, as illustrated, is disposed at an angle of about 30° with respect to the plane 264 on which the central longitudinal axis 266 of the main body 202 lies. In other embodiments, however, each ramp angle may be angled to any degree with respect to the plane 264 on which the central longitudinal axis 266 of the main body 202 lies. For example, ramp angles of between about 15° and about 45° are considered suitable. Ramp angles between about 20° and about 45° are also considered suitable. Ramp angles between about 20° and about 40° are also considered suitable. Ramp angles greater than about 20° and less than about 40° are also considered suitable. Ramp angles between about 25° and about 35° are also considered suitable. Ramp angles greater than about 25° and less than about 35° are also considered suitable. An individual ramp angle can have the same or a different angular measurement from any other ramp angle. In alternative embodiments, the anchor passageways may define a total of zero, one, two, three, four, or more than four ramps. A skilled artisan will be able to determine suitable sizes and shapes of the ramps and suitable ramp angles based on a variety of factors, including the size of the plate, the size of the locking members, and the size of the anchors.

The main body 202 also defines locking member openings 224, 226, 228, and 230. Each locking member opening 224, 226, 228, and 230 defines a locking member passageway, represented by the reference number of the respective locking member opening increased by 8, that extends between the first 204 and second 206 sides. Thus, the main body 202 has four locking member passageways 232, 234, 236, and 238. Each of the locking member passageways 232, 234, 236, and 238 has an upper portion, represented by the reference number of the respective locking member passageway followed by 'a', and a lower portion, represented by the reference number of the respective locking member passageway followed by 'b'. For each of the locking member passageways 232, 234, 236, and 238, the upper portion is in communication with the adjacent one of the anchor passageways 216, 218, 220, and 222 and the lower portion is in communication with one of the pin passageways 250, 252, 254, 256, which are described below. Thus, locking member passageway 232 has an upper portion 232a and a lower portion 232b. The upper portion 232a is in communication with adjacent anchor passageway 216 and the lower portion 232b is in communication with pin passageway 250. Locking member passageway 234 has an upper portion 234a and a lower portion 234b. The upper portion 234a is in communication with anchor passageway 218 and the lower portion 234b is in communication with pin passageway 252. Locking member passageway 236 has an upper portion 236a and a lower portion 236b. The upper portion 236a is in communication with anchor passageway 220 and the lower portion 236b is in communication with pin passageway 254. Locking member passageway 238 has an upper portion 238a and a lower portion 238b. The upper portion 238a is in communication with anchor passageway 222 and the lower portion 238b is in communication with pin passageway 256.

The main body 202 has a side 240 that bounds the main body 202 and extends between the first 204 and second 206 sides. The main body 202 also defines pin openings 242, 244, 246, 248 on the side 240. Each pin opening 242, 244, 246, 248 is in communication with a pin passageway, represented by the reference number of the respective pin opening increased by 8, that extends from the side 240 and into the main body 202. Two pin openings 242, 244 and pin passageways 250, 252 are located on a first side of the main body 202, and two pin openings 246, 248 and pin passageways 254, 256 are located on a second, opposite side of the main body 202 in the same position as pin openings 242, 244 and pin passageways 250, 252. Each of the pin passageways 250, 252, 254, 256 is also in communication with one of the locking member passageways 232, 234, 236, and 238. Thus, each of the pin passageways 250, 252, 254, 256 provides a passageway extending from one of the pin openings 242, 244, 246, 248 on the side 240 of the main body and to one of the locking member passageways 232, 234, 236, 238. This configuration facilitates insertion of pins 500a, 500b, 500c, and 500d into the respective pin passageways 250, 252, 254, 256 while also allowing the pins 500a, 500b, 500c, 500d to interact with the locking members 400a, 400b, 400c, 400d in the desired manner, as described below.

Osteosynthesis system 100 includes anchors 300a, 300b, 300c, and 300d. Each of the anchors 300a, 300b, 300c, and 300d is disposed in one of the anchor passageways 216, 218, 220, and 222.

Osteosynthesis system 100 includes locking members 400a, 400b, 400c, and 400d. Each of the locking members 400a, 400b, 400c, 400d is disposed in one of the locking member passageways 232, 234, 236, and 238. As described in detail below, each of the locking members 400a, 400b, 400c, 400d is secured within one of the locking member passageways 232, 234, 236, and 238, but is rotatable within its respective locking member passageway 232, 234, 236, and 238.

Figure 8:
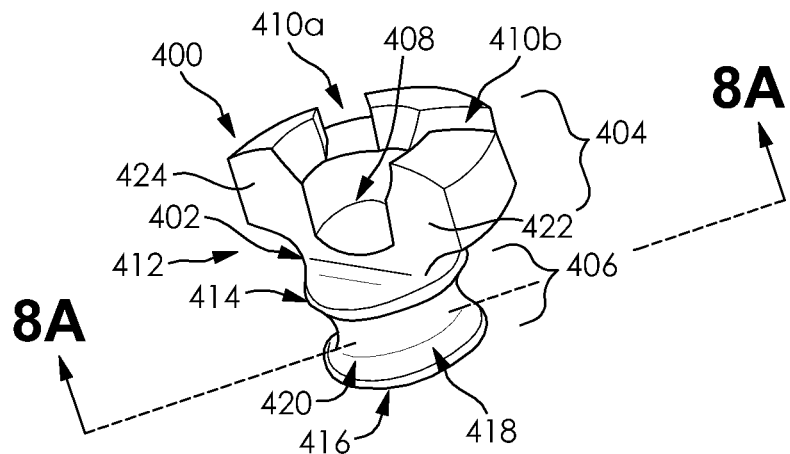
FIG. 8 is a magnified view of one locking member of the osteosynthesis system illustrated in FIG. 1.
Figure 9B:
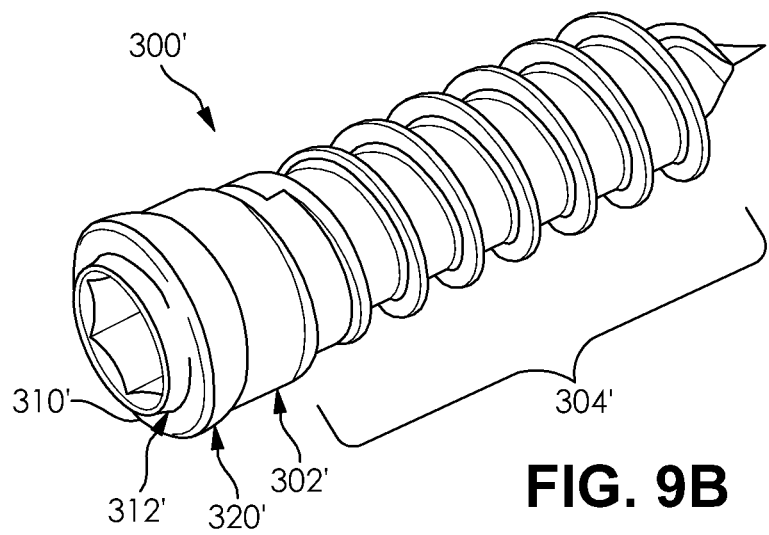
FIG. 9B is a perspective view of an alternative anchor.

As best illustrated in FIG. 8, a locking member 400 has a main body 402 that defines an upper portion 404 and a lower portion 406. The upper portion 404 comprises a partial disc-shaped structure that defines a central recess 408 and slots 410a and 410b. As a partial disc-shaped structure, the upper portion 404 leaves a void 412 where the remainder of the disc-shaped structure would be located if included. The lower portion 406 defines upper 414 and lower 416 ends and a circumferential groove 418 disposed between the upper 414 and lower 416 ends. In the illustrated embodiment, the circumferential groove 418 is defined by a u-shaped wall 420 formed by the lower portion 406 of the locking member 400. Each of the slots 410a, 410b is positioned slightly inward in the upper portion 404 of a position opposite one of the ends 422, 424 defined by the upper portion 404 with respect to a central longitudinal axis of the locking member 400. This facilitates use of a tool, such as a screwdriver, in the slots 410a, 410b to rotate the locking member 400 within one of the locking member passageways 232, 234, 236, and 238 despite the absence of a portion of the disc-shaped member that would be disposed within the void 412 if the upper portion 404 defined a complete disc-shaped member.

Figure 8A:
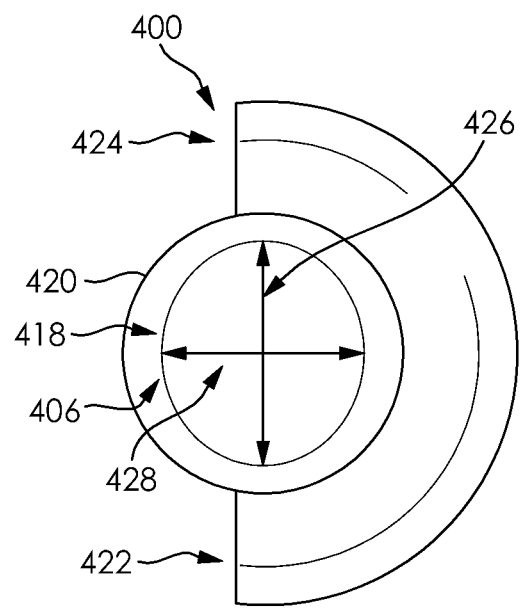
FIG. 8A is a magnified sectional view of the locking member illustrated in FIG. 8, taken along line 8A-8A.

As best illustrated in FIG. 8A, the lower portion 406 of the locking member 400 has a non-circular cross-sectional shape that defines major 426 and minor 428 axes. This gives the circumferential groove 418 a non-circular path as it extends around the lower portion 406 of the locking member 400. Also, as described below, this structure interacts with one of the pins 500a, 500b, 500c, 500d to provide one or more stop positions for the locking member 400 as it is rotated within one of the locking member passageways 232, 234, 236, and 238 defined by the plate 200. Any suitable non-circular cross-sectional shape can be used in a locking member according to a particular embodiment, and a skilled artisan will be able to select an appropriate non-circular cross-sectional shape for a particular locking member based on various considerations, including the relative ease with which the locking member should be able to be rotated within a locking member passageway of a plate in a particular osteosynthesis system. Examples of suitable non-circular cross-sectional shapes include ovoid, substantially ovoid, faceted, and polygonal cross-sectional shapes. For ovoid cross-sectional shapes, an ovoid shape having any suitable ratio between major and minor axes can be used. Thus, any ratio of the major axis of an ovoid shape to the minor axis of the ovoid shape that is greater than 1 can be used. It is noted that a circular cross-sectional shape can be used, if desired. In these embodiments, the ratio of the major axis to the minor axis is equal to 1 or substantially equal to 1. It is noted that, no matter the cross-sectional shape used, a locking member is advantageously configured so that it can be rotated in either a clockwise or counter-clockwise direction. Furthermore, it is considered advantageous for a locking member to be configured so that it can be rotated in either direction from an initial position, in which an associated anchor is not secured by the locking member, to a second position, in which the associated anchor is secured by the locking member, and then, in the same direction, to the initial position again, in which the associated anchor is not secured by the locking member.

As best illustrated in FIG. 5, the void 412 provided by the structure of the upper portion 404 of each of the locking members 400a, 400b allows an anchor to be passed into the respective anchor passageway 216, 218 at an angle $\alpha_1$, $\alpha_2$ while the locking members 400a, 400b are in a first, or unlocked, position. As described in detail below, once an anchor is passed into an anchor passageway 216, 218 in this manner, the respective locking member 400a, 400b can be rotated within its respective locking member passageway 224, 226 to engage the anchor and lock the anchor in the anchor passageway 216, 218. Without the partial disc-shaped member structure of the upper portion 404 of the locking members 400a, 400b, the locking members 400a, 400b would interfere with this placement of the anchors. As a result of the partial disc-shaped structure of the upper portion 404 of the locking member 400a, 400b, the anchors 300a, 300b, 300c, 300d can be placed at greater angles than those in conventional osteosynthesis systems. Indeed, this structure enables to anchors to achieve hyperangulation as compared to conventional osteosynthesis systems. As indicated above, the anchors in an osteosynthesis system according to a particular embodiment can be disposed at any suitable angle with respect to a central longitudinal axis of the plate in the particular osteosynthesis system, and a skilled artisan will be able to select an appropriate angle based on various considerations, including the location at which the particular osteosynthesis system is intended to be implanted. The angle can be varied through a combined manipulation of the axis on which the anchor passageways are disposed and the size and configuration of the upper portion of the locking members in the particular osteosynthesis system. The inventors have determined that angles of between about 15° and about 45° are considered suitable. Angles between about 20° and about 45° are also considered suitable. Angles between about 20° and about 40° are also considered suitable. Angles greater than about 20° and less than about 40° are also considered suitable. Angles between about 25° and about 35° are also considered suitable. Angles greater than about 25° and less than about 35° are also considered suitable. An angle of about 30° is also considered suitable. Indeed, an osteosynthesis system in which each of the anchor passageways and locking members are configured such that each anchor lies on a plane that is disposed at an angle of about 30° to a plane containing the central longitudinal axis of the main body of the plate of the osteosynthesis system is considered particular advantageous. As noted above, the angles can in a particular osteosynthesis system can be exactly the same or different from each other. It is considered advantageous to have a first set of anchor passageways and locking members disposed on a first end of a plate configured such that each of the anchors passed into these anchor passageways lies on a plane that is disposed at an angle of about 30° to a plane containing the central longitudinal axis of the main body of the plate of the osteosynthesis system, and a second set of anchor passageways and locking members disposed on a second, opposite end of the plate configured such that each of the anchors passed into these anchor passageways lies on a plane that is disposed at an angle of about −30° to a plane containing the central longitudinal axis of the main body of the plate of the osteosynthesis system.

Osteosynthesis system 100 includes four pins 500*a*, 500*b*, 500*c*, 500*d*. Each of the pins 500*a*, 500*b*, 500*c*, 500*d* is disposed in one of the pin passageways 250, 252, 254, 256. As described in detail below, each of the pins 500*a*, 500*b*, 500*c*, 500*d* engages one of the locking members 400*a*, 400*b*, 400*c*, 400*d* that is disposed in the one of the locking member passageways 232, 234, 236, 238 that is in communication with the one of the pin passageways 250, 252, 254, 256 within which the one of the pins 500*a*, 500*b*, 500*c*, 500*d* is disposed. As best illustrated in FIGS. 5 and 6, each of the pins 500*a*, 500*b* is disposed in the circumferential groove 418 defined by the locking member 400*a*, 400*b* that is adjacent the respective pin 500*a*, 500*b*. As such, each of the pins 500*a*, 500*b* engages the respective adjacent locking member 400*a*, 400*b*.

As best illustrated in FIG. 7A, a pin 500 comprises a coiled sheet defining a main body 502 extending between first 504 and second 506 ends. In the illustrated embodiment, each of the ends 504, 506 defines a taper 508, 510 on the outer surface 512. The inclusion of one or both tapers 508, 510 facilitates placement of the pin 500 in a pin passageway of a plate of an osteosynthesis system.

A pin comprising a coiled sheet in an osteosynthesis system according to a particular embodiment can comprise any suitable number of coils or portions of coils, and a skilled artisan will be able to select an appropriate number of coils or portions of coils for a pin an a particular osteosynthesis system based on various considerations, including any desired rigidity and/or deformability of the pin. As best illustrated in FIG. 7A, a pin comprising a sheet of material rolled to form a single coil of the sheet is considered suitable. A partial coil, or more than a single coil is also considered suitable.

Furthermore, a pin in an osteosynthesis system according to a particular embodiment can comprise any suitable, and a skilled artisan will be able to select an appropriate structure for a pin in a particular osteosynthesis system based on various considerations including any desired rigidity and/or deformability of the pin. Examples of suitable structures include a coiled sheet, a rod, and a slit tube. FIG. 7B illustrates an alternative pin 500' that comprises a slit tube. The pin 500' comprises a main body 502' extending between first 504' and second 506' ends. In the illustrated embodiment, each of the ends 504', 506' defines a taper 508', 510' on the outer surface 512'. The main body 502' defines an elongate slit 514' that extends along the entire length of the pin 500', from the first end 504' to the second end 506'. In general, a pin comprising a slit tube, such as pin 500', is relatively more rigid than a pin comprising a coiled sheet, such as pin 500 illustrated in FIG. 7A, but is relatively easier to deform permanently. Thus, use of a pin comprising a slit tube, such as pin 500', may be advantageous in osteosynthesis systems in which a greater degree of tactile feedback is desired in response to rotation of a locking members, which are engaged with the pins, even though a permanent deformation of the pin may result. It is noted that pins comprising different structures can be used within a single osteosynthesis system to achieve different types and degrees of tactile feedback in response to rotation of respective engaged locking members in the osteosynthesis system.

Figure 7C:
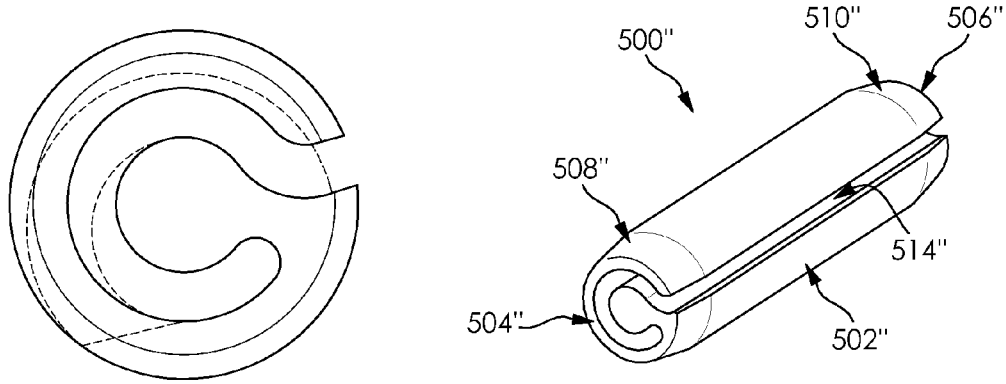
FIG. 7C is a magnified view of another alternative pin.

FIG. 7C illustrates another alternative pin 500".

Osteosynthesis system 100 includes four anchors 300*a*, 300*b*, 300*c*, 300*d*. Each of the anchors 300*a*, 300*b*, 300*c*, 300*d* is disposed in one of the anchor passageways 216, 218, 220, 222. As described above, each of the anchors 300*a*, 300*b*, 300*c*, 300*d* is adapted to be engaged by one of the locking members 400*a*, 400*b*, 400*c*, 400*d* that is disposed in the one of the locking member passageways 232, 234, 236, 238 that is in communication with the one of the anchor passageways 216, 218, 220, 222 within which the one of the anchors 300*a*, 300*b*, 300*c*, 300*d* is disposed. Each of the anchor passageways 216, 218, 220, 222 is sized and configured to receive one of the anchors 300*a*, 300*b*, 300*c*, 300*d* such that the one of the anchors 300*a*, 300*b*, 300*c*, 300*d* is seated in the one of the anchor passageways 216, 218, 220, 222 and mechanically stopped from passing completely through the one of the anchor passageways 216, 218, 220, 222 by the plate 200. Furthermore, each of the anchor passageways 216, 218, 220, 222 is sized and configured such that the one of the locking members 400*a*, 400*b*, 400*c*, 400*d* that is disposed in the one of the locking member passageways 232, 234, 236, 238 that is in communication with the one of the anchor passageways 216, 218, 220, 222 is rotatable within the one of the locking member passageways 232, 234, 236, 238 such that the upper portion 404 of the one of the locking members 400*a*, 400*b*, 400*c*, 400*d* engages the one of the anchors 300*a*, 300*b*, 300*c*, 300*d* disposed in the anchor passageway 216, 218, 220, 222 but does not cover the top of the anchor 300*a*, 300*b*, 300*c*, 300*d*.

FIG. 9A illustrates an anchor 300 suitable for use in an osteosynthesis system according to a particular embodiment. The anchor 300 is an elongate member having a head 302 and a shank 304. In the illustrated embodiment, the head 302 defines top surface 306, a recess 308 and a circumferential ridge 310 that is distal to the top surface 306. As such, the head 302 defines a circumferential shoulder 312. As best illustrated in FIGS. 10E, 10F, 10G, and 10H, the circumferential shoulder 312 provides a structure distal to the top surface 306 of the head 302 that is adapted to be engaged by the top portion 404 of a locking member 400*a* as the locking member 400*a* is rotated within a locking member passageway 232 disposed adjacent the anchor passageway 216 within which the anchor 300*a* is disposed. When engaged by the locking member 400*a* in this manner, the top surface 306 and the recess 308 of the head 302 are free of the locking member 400*a*. This configuration enables the anchor 300*a* to be driven with a tool matingly disposed in the recess 308 even after the locking member 400*a* has been rotated to engage the anchor 300*a*.

The shank 304 defines a helical plane 314 that facilitates securement of the anchor 300 to a member, such as a bone or a member formed of another material, such as wood or plastic. In the illustrated embodiment, the helical plane 314 has a proximal portion 316 with a first pitch and a distal portion 318 with a second pitch. It is noted that the anchor 300 can include a shank having any suitable structure that allows the anchor 300 to perform as described herein. Inclusion of a helical plane is considered optional. Non-limiting examples of other suitable structures that can be defined by the shank of the anchor include a nail-like structure and a barbed member. Similarly, the anchor in an osteosynthesis system according to a particular embodiment can include a head having any suitable structure that allows the anchor to perform as described herein. Non-limiting examples of other suitable structures include a spherical body, a cube, and a block.

Fixed angle anchors, such as anchor 300 illustrated in FIG. 9A, are suitable for use with osteosynthesis systems. It is noted, though, that other types of anchors can be used. For example, FIG. 9B illustrates a variable angle anchor 300' suitable for use with an osteosynthesis system according to a particular embodiment. The anchor 300' includes spherical head 302' and a head assembly 320' attached to the head 302'. The head assembly 320' freely rotates about the head 302' to dispose a recess adapted for receiving a tool at an angle to the shank 304'. The head assembly 320' defines a circumferential ridge 310' to provide a circumferential shoulder 312' as described above for the anchor 300 illustrated in FIG. 9A.

Each of FIGS. 10A, 10B, 10C, 10D, 10E, 10F, 10G, and 10H illustrates a portion of the osteosynthesis system 100 in various configurations achieved during use. FIGS. 10A and 10E illustrate a portion of the osteosynthesis system 100 in a first configuration. In this configuration, the locking member 400a is in an initial position, reflecting a 0° rotation from its initial position. In this configuration, the major axis 426 of the lower portion 406 of the locking member 400a is disposed substantially parallel to a lengthwise axis of the pin 500a that is adjacent the locking member 400a. Also, the top portion of the locking member 400a is not engaged with the circumferential shoulder 312 of the anchor 300a. As such, in this configuration, the anchor 300a can be removed from the plate 200, if desired.

FIGS. 10B and 10F illustrate a portion of the osteosynthesis system 100 in a second configuration. In this configuration, the locking member 400a is in a rotated position, reflecting a 45° rotation from its initial position. In this configuration, both the major axis 426 and the minor axis 428 of the lower portion 406 of the locking member 400a are disposed at an intersecting angle to a lengthwise axis of the pin 500a that is adjacent the locking member 400a. As a result, as best illustrated in FIG. 10B, the lower portion 406 of the locking member 400a exerts a downward force on the pin 500a as the locking member 400a is rotated into this position. The top portion of the locking member 400a has not, however, engaged the circumferential shoulder 312 of the anchor 300a. As such, in this configuration, the anchor 300a can be removed from the plate 200, if desired.

FIGS. 10C and 10G illustrate a portion of the osteosynthesis system 100 in a third configuration. In this configuration, the locking member 400a is in a rotated position, reflecting a 90° rotation from its initial position. In this configuration, the major axis 426 of the lower portion 406 of the locking member 400a is disposed at a substantially perpendicular angle to a lengthwise axis of the pin 500a that is adjacent the locking member 400a. As a result, as best illustrated in FIG. 10C, the lower portion 406 of the locking member 400a continues to exert a downward force on the pin 500a as the locking member 400a is rotated into this position. As best illustrated in FIG. 10G, the top portion of the locking member 400a has partially engaged the circumferential shoulder 312 of the anchor 300a as a result of rotating into this position. As such, in this configuration, the anchor 300a cannot be removed from the plate 200.

FIGS. 10D and 10H illustrate a portion of the osteosynthesis system 100 in a fourth configuration. In this configuration, the locking member 400a is in a rotated position, reflecting a 180° rotation from its initial position. In this configuration, the major axis 426 of the lower portion 406 of the locking member 400a is, again, disposed substantially parallel to a lengthwise axis of the pin 500a that is adjacent the locking member 400a. In this configuration, the major axis 426 is disposed in an opposite orientation than it was in the initial position illustrated in FIGS. 10A and 10E. As a result, as best illustrated in FIG. 10D, the pin 500a, due to its coiled structure, exerts an upward force on lower portion 406 of the locking member 400a as the locking member 400a is rotated into this position. As best illustrated in FIG. 10H, the top portion of the locking member 400a has fully engaged the circumferential shoulder 312 of the anchor 300a as a result of rotating into this position. As such, in this configuration, the anchor 300a cannot be removed from the plate 200.

This rotational movement and engagement of an anchor can be repeated for each of the locking members included in an osteosynthesis system according to a particular embodiment. Furthermore, the rotational movement can be reversed if adjustment and/or removal of an anchor is desired.

Figure 11A:
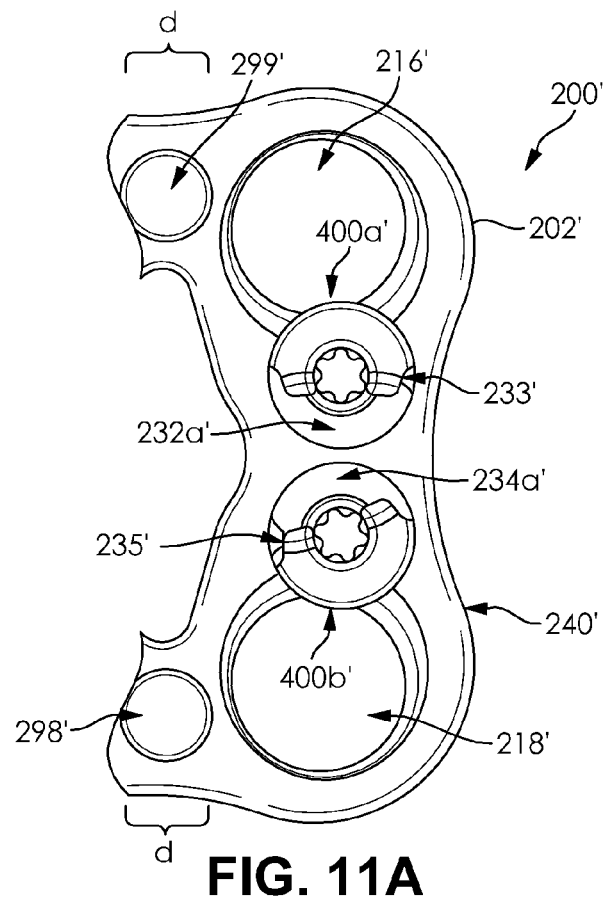
FIG. 11A is a partial top view of an alternative plate and two locking members.
Figure 11B:
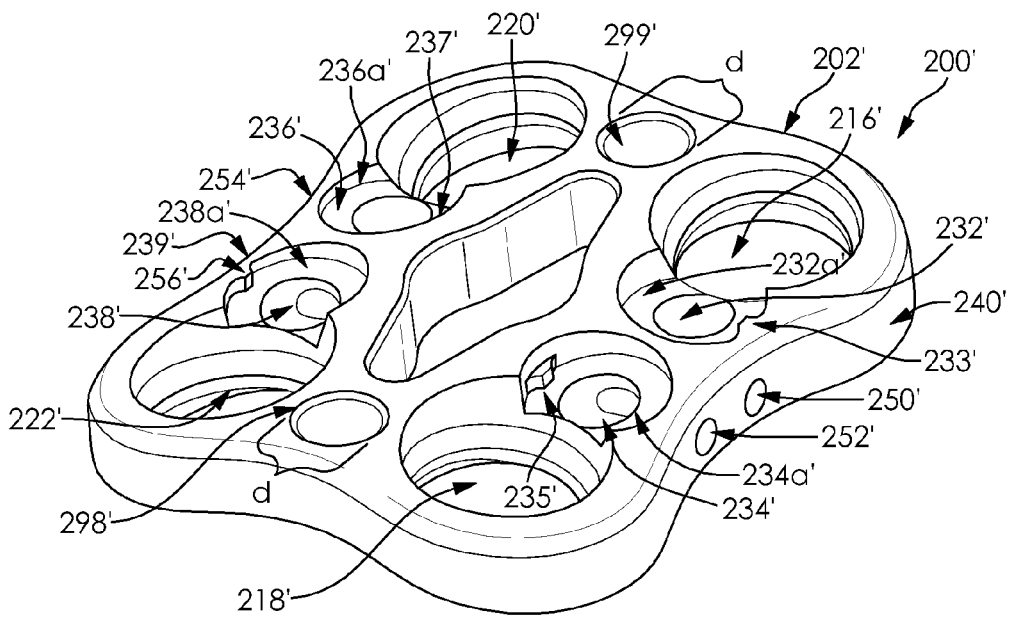
FIG. 11B is a perspective view of the plate illustrated in FIG. 11A. The plate is illustrated independent of the locking members.
Figure 11C:
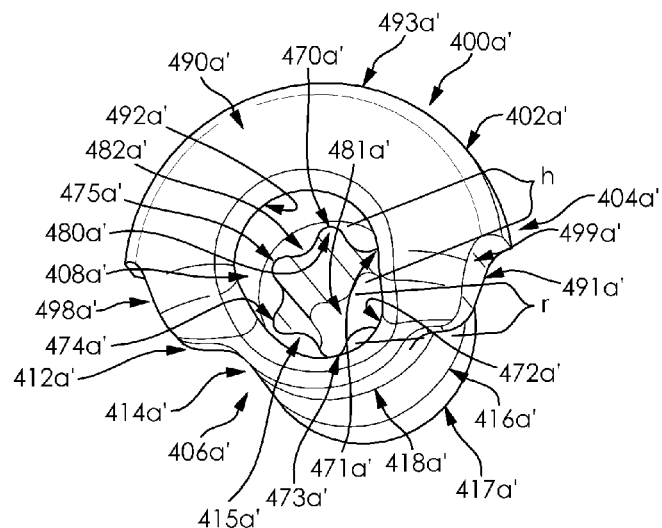
FIG. 11C is a perspective view of a locking member illustrated in FIG. 11A. The locking member is illustrated independent of the plate.

FIGS. 11A, 11B, and 11C illustrate components of another osteosynthesis system. FIG. 11A illustrates an alternative plate 200' and locking members 400a', 400b'. FIG. 11B illustrates the alternative plate 200' independent of the locking members shown in FIG. 11A. FIG. 11C illustrates an alternative locking member 400a' independent of the plate 200' shown in FIG. 11B. The alternative osteosynthesis system is similar to the osteosynthesis system 100 described above, except as described below. Thus, the alternative osteosynthesis system includes the plate 200', a set of anchors (not illustrated in FIG. 11A or 11B), a set of locking members 400a', 400b', and others not illustrated in FIGS. 11A and 11B, and a set of pins (not illustrated in FIG. 11A, 11B, or 11C).

The plate 200' has a main body 202' that defines three sets of passageways: anchor passageways 216', 218', 220', 222'; locking member passageways 232', 234', 236', 238'; and pin passageways 250', 252', 254', 256'. Each of the locking member passageways 232', 234', 236', 238' partially intersects one of the anchor passageways 216', 218', 220', 222'. Each of the pin passageways 250', 252', 254', 256' provides a passageway extending from the side 240' of the main body 202' of the plate 200' to one of the locking member passageways 232', 234', 236', 238'. Each of the anchors is disposed in one of the anchor passageways 216', 218', 220', 222'. Each of the locking members is disposed in one of the locking member passageways 232', 234', 236', 238' and is rotatable within the respective one of the locking member passageways 232', 234', 236', 238'. Each of the pins is disposed in one of the pin passageways 250', 252', 254', 256'. Upper portions 232a', 234a', 236a', 238a' include stop members 233', 235', 237', 239'. The plate 200' also defines a lower cavity 298' and an upper cavity 299'. The lower and upper cavities 298', 299' each define a diameter d.

FIG. 11A best illustrates the stop members 233', 235' as configured to mate with an individual locking member 400a', 400b' to prevent the axial advancement of an individual locking member 400a', 400b' past a particular, fully advanced position. FIG. 11B best illustrates each stop member 233', 235', 237', 239' protruding from its respective upper portion 232a', 234a', 236a', 238a' toward the locking member passageways 232', 234', 236', 238' adjacent each upper portion 232a', 234a', 236a', 238a'. Two stop members 233', 239' are defined by two upper portions 232a', 238a'. The stop members 233', 239' are an integral part of their respective upper portions 232a', 238a'; that is, they are formed as a part of the plate 200' itself. The remaining stop members 235', 237', on the other hand, are disposed on the two remaining upper portions 234a', 236a'. These stop members 235', 237' are not formed integrally with the upper portions 234a', 236a' and, instead, are mounted on their respective upper portions 234a', 236a' via an adhesive. Other potential methods of mounting the stop members 235', 237' include through the use of welding, sewing, a staple, a magnet, a hook, or any other suitable technique. In another embodiment, each stop member may be mounted to its respective upper portion. In a different embodiment, each stop member may be integrally formed with and defined by its respective upper portion. In alternative embodiments, any of zero, one, two, three, four, or more than four stop members may be defined by or disposed on any of upper portions. A skilled artisan will be able to determine whether it is suitable to include one or more stop members based on a variety of factors, including the size of the plate, the size of the locking members, and the size of the anchors.

As also best illustrated in FIG. 11B, two of the stop members 233', 239' are positioned closer to the side 240' than are the other two stop members 235', 237'. However, each stop member 233', 235', 237', 239' may be positioned at any distance from the side 240'. Thus, for example, in another embodiment, each of the stop members 233', 235', 237', 239' may be equidistant from the side 240'. An individual stop member also may be positioned further from or closer to the side than any other stop member in a different embodiment. A skilled artisan will be able to suitably position each stop member based on a variety of factors, including the size of the plate, the size of the locking members, and the size of the anchors.

Each stop member 233', 235', 237', 239' has a substantially trapezoidal cross-sectional shape in the illustrated embodiment. In addition, each stop member 233', 235', 237', 239' is the same size as each other stop member 233', 235', 237', 239'. In an alternative embodiment, one or more stop members may have a different cross-sectional shape than any other stop member; suitable cross-sectional shapes include circular, triangular, square, rectangular, pentagonal, or any other shape. Furthermore, in a different embodiment, one or more stop members may be smaller than or larger than any other stop member. Thus, an individual stop member, for example, may be larger than stop member, but smaller than stop member. A skilled artisan will be able to determine suitable sizes and cross-sectional shapes of each stop member based on a variety of factors, including the size of the plate, the size of the locking members, and the size of the anchors.

The plate 200' defines a lower cavity 298' and an upper cavity 299', as illustrated in FIGS. 11A and 11B. The lower and upper cavities 298', 299' assist in alignment of the plate 200' prior to the placement of the anchors. In the illustrated embodiment, the lower cavity 298' is disposed between two anchor passageways 218', 222', while the upper cavity 299' is disposed between the two other anchor passageways 216', 220'. Each of the lower and upper cavities 298', 299' has a circular cross-sectional shape and, furthermore, the lower cavity 298' and the upper cavity 299' have equal diameters d. In another embodiment, each of the lower cavity and the upper cavity may be disposed at any other location on the plate. In a different embodiment, the plate may only define an upper cavity. The lower and upper cavities may also have any cross-sectional shape, including triangular, square, rectangular, elliptical, pentagonal, or any other shape. Additionally, the lower cavity may have a diameter that is greater than or less than the diameter of the upper cavity. A skilled artisan will be able to determine a suitable placement of, diameter of, and cross-sectional shape of the lower and upper cavities based on a variety of factors, including the size of the plate, the size of the locking members, and the size of the anchors.

FIG. 11C illustrates a locking member 400a' having a main body 402a' that defines an upper portion 404a' and a lower portion 406a'. The upper portion 404a' comprises a partial disc-shaped structure that defines a central recess 408a' and leaves a void 412a' where the remainder of the disc-shaped structure would be located if included. The upper portion 404a' also includes an upper surface 490a', a lower surface 491a', an inner edge 492a', an outer edge 493a', and rounded shoulders 498a', 499a'. The lower portion 406a' defines upper 414a' and lower 416a' ends and a circumferential groove 418a' disposed between the upper 414a' and lower 416' ends. In addition, the upper end 414a' defines an upper surface 415' and the lower end 416a' defines a lower surface 417a'. The lower portion 406a' also defines a star having curvilinear surface 480a' defining a continuously undulating perimeter 482a', a channel 481a' having a height h defined by the star having a curvilinear surface 480a', and six curved sections 470a', 471a', 472a', 473a', 474a', 475a' each having a radius r.

As best illustrated in FIG. 11C, the rounded shoulders 498a', 499a' defined by the upper portion 404a' are configured to mate with a stop member (not illustrated in FIG. 11C) to prevent the axial advancement of the locking member 400a' past a particular, fully advanced position. The rounded shoulders are integrally formed with the upper portion 404a' of the locking member 400a' and extend from the upper surface 490a' of the upper portion 404a' to the lower surface 491a' of the upper portion 404a'. Furthermore, the rounded shoulders 498a', 499a' are defined by the outer edge 493a' of the upper portion 414a' and are substantially opposite the inner edge 492a' about the upper portion 404a'. Though the embodiment illustrated in FIG. 11C illustrates two rounded shoulders 498a', 499a', in another embodiment the upper portion may define only one rounded shoulder. Moreover, in a different embodiment, a locking member may not define any rounded shoulders. A skilled artisan will be able to determine suitable rounded shoulders based on a variety of factors, including the size of the plate, the size of the locking members, and the size of the anchors.

FIG. 11C also best illustrates a star having a curvilinear surface 480a' defined by the lower portion 406a'. The star having a curvilinear surface 480a' has a continuously undulating perimeter 482a' that defines six curved sections 470a', 471a', 472a', 473a', 474a', 475a'. Each curved section 470a', 471a', 472a', 473a', 474a', 475a' defines a radius r that is equal to the radius of each other section 470a', 471a', 472a', 473a', 474a', 475a'. Additionally, each curved section 470a', 471a', 472a', 473a', 474a', 475a' is equidistant from its two adjacent curved sections 470a', 471a', 472a', 473a', 474a', 475a'. In other embodiments, one or more curved sections may have a different radius than one or more other curved sections. For example, the radius of curved section may be greater than the radius of a second curved section, but less than the radius of a third curved section. In alternative embodiments, one or more curved sections may not be equidistant from one or more other curved sections. In different embodiments, the perimeter may be circular, elliptical, triangular, square, rectangular, or any other shape. A skilled artisan will be able to determine suitable sizes, shapes, and radii of the curved sections based on a variety of factors, including the size of the plate, the size of the locking members, and the size of the anchors.

The star having a curvilinear surface 480a' defines a channel 481a', as FIG. 11C best illustrates. The channel 481a' extends through the upper and lower ends 414a', 416a' of the lower section 406a' from the upper surface 415a' to the lower surface 417a'. The star having a curvilinear surface 480a' defines a height h, which also extends from the upper surface 415a' to the lower surface 417a' in the illustrated embodiment. In a different embodiment, the star having a curvilinear surface may have a height that is less than the distance between the upper surface and the lower surface. In another embodiment, the star having a curvilinear surface may be partially or fully defined by the upper portion. A skilled artisan will be able to determine a suitable height of the star having a curvilinear surface based on a variety of factors, including the size of the plate, the size of the locking members, and the size of the anchors.

Each of FIGS. 11, 12, 13A, 13B, 14A, and 14B illustrates another osteosynthesis system 1100 or one or more components thereof. The illustrated osteosynthesis system 1100 is similar to the osteosynthesis system 100 described above, except as described below. Thus, osteosynthesis system 1100 includes a plate 1200, a set of anchors 1300a, 1300b, 1300c, 1300d, a set of locking members 1400a, 1400b, 1400c, 1400d, and a set of pins 1500a, 1500b, 1500c, 1500d. The plate 1200 defines three sets of passageways: anchor passageways 1216, 1218, 1220, 1222; locking member passageways 1232, 1234, 1236, 1238; and pin passageways 1250, 1252, 1254, 1256. Each of the locking member passageways 1232, 1234, 1236, 1238 partially intersects one of the anchor passageways 1216, 1218, 1220, 1222. Each of the pin passageways 1250, 1252, 1254, 1256 provides a passageway extending from the side 1240 of the main body 1202 of the plate 1200 to one of the locking member passageways 1232, 1234, 1236, 1238. Each of the anchors 1300a, 1300b, 1300c, 1300d is disposed in one of the anchor passageways 1216, 1218, 1220, 1222. Each of the locking members 1400a, 1400b, 1400c, 1400d is disposed in one of the locking member passageways 1232, 1234, 1236, 1238 and is rotatable within the respective one of the locking member passageways 1232, 1234, 1236, 1238. Each of the pins 1500a, 1500b, 1500c, 1500d is disposed in one of the pin passageways 1250, 1252, 1254, 1256.

Figure 12:
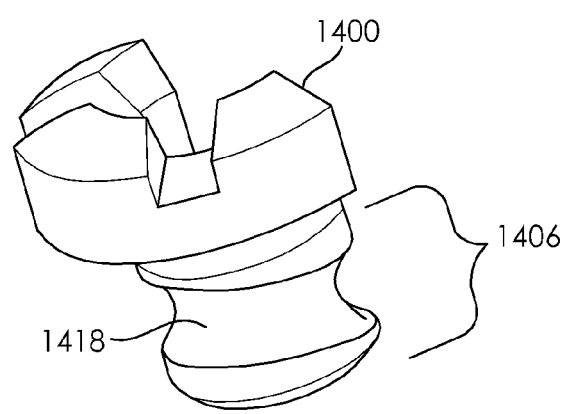
FIG. 12 is a magnified view of one locking member of the osteosynthesis system illustrated in FIG. 11.

In this embodiment, and as best illustrated in FIG. 12, the locking member 1400 defines a circumferential groove 1418 that extends around the circumference of the lower portion 1406 of the locking member 1400 at an intersecting angle to a central longitudinal axis of the locking member 1400. As a result of this configuration, the locking member 1400 telescopes inwardly and outwardly as the locking member 1400 is rotated within one of the locking member passageways 1232, 1234, 1236, 1238 and is engaged by one of the pins 1500a, 1500b, 1500c, 1500d.

Figure 13A:
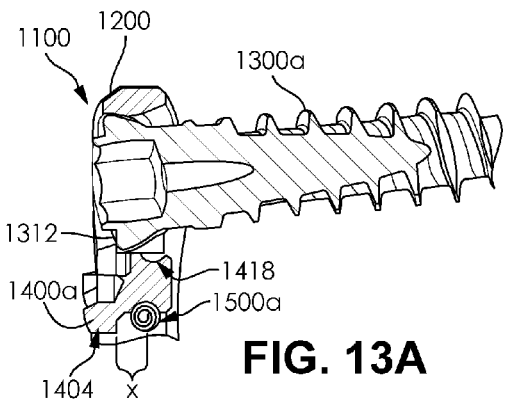
FIG. 13A is a magnified partial sectional view of the osteosynthesis system illustrated in FIG. 11. The locking member is shown in a first configuration.
Figure 13B:
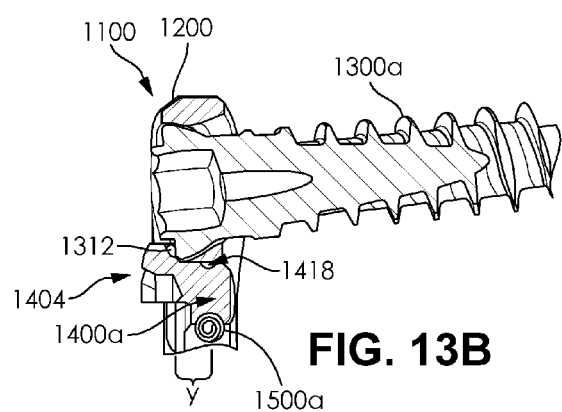
FIG. 13B is a magnified partial sectional view of the osteosynthesis system illustrated in FIG. 11. The locking member is shown in a second configuration.
Figure 11:
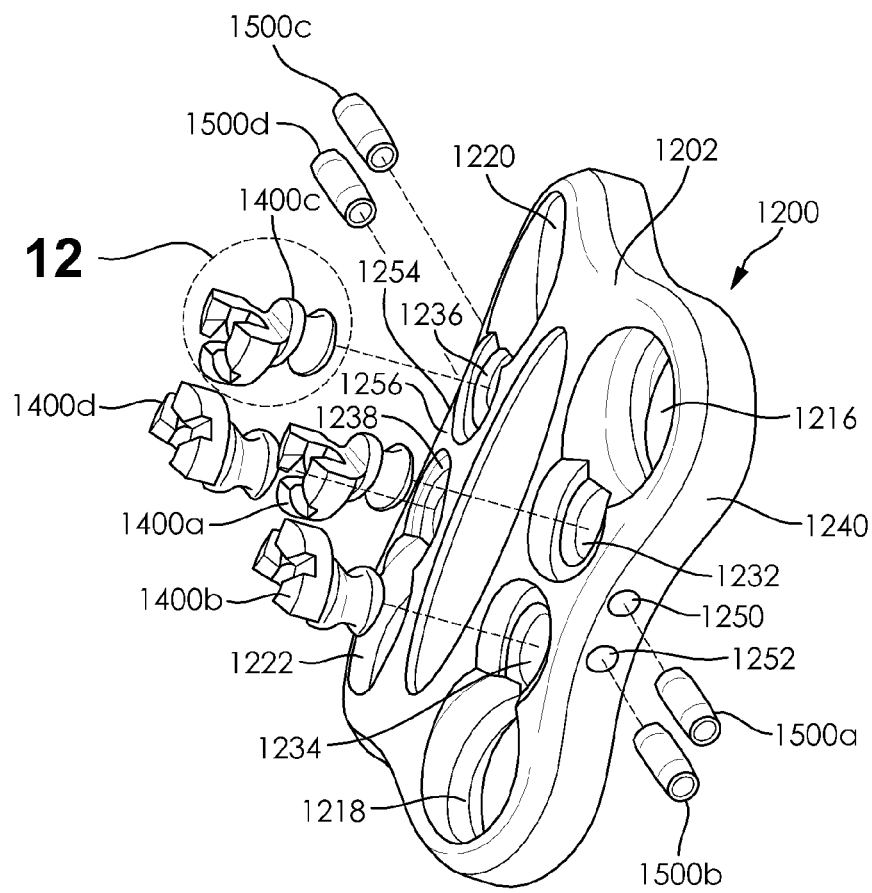
FIG. 11 is an exploded view of another osteosynthesis system.

Each of FIGS. 13A and 13B illustrates a portion of the osteosynthesis system 1100 in configurations achieved during use. FIG. 13A illustrates a portion of the osteosynthesis system 1100 in a first configuration. In this configuration, the locking member 1400a is in an initial position, reflecting a 0° rotation from its initial position. In this configuration, the top portion 1404 of the locking member 1400a is not engaged with the circumferential shoulder 1312 of the anchor 1300a. As such, in this configuration, the anchor 1300a can be removed from the plate 1200, if desired. The angled configuration of the circumferential groove 1418 is evident in the Figure. FIG. 13B illustrates a portion of the osteosynthesis system 1100 in a second configuration. In this configuration, the locking member 1400a is in a rotated position, reflecting a 180° rotation from its initial position. In this configuration, the top portion 1404 of the locking member 1400a has fully engaged the circumferential shoulder 1312 of the anchor 1300a as a result of rotating into this position. As such, in this configuration, the anchor 1300a cannot be removed from the plate 1200.

The effect of the angled circumferential groove 1418 is illustrated by comparing FIG. 13A to FIG. 13B. In FIG. 13A, when the locking member 1400a is in its first or initial position, the distance between the central axis of the pin 1500a, which is disposed within a portion of the circumferential groove 1418, is represented by the letter x. In FIG. 13B, when the locking member 1400a is in its second or locking position, the distance between the central axis of the pin 1500a, which is disposed within another portion of the circumferential groove 1418, is represented by the letter y. The distance y is greater than the distance x, such that the locking member 1400 has telescoped in an outwardly direction as a result of the pin 1500a traveling through the circumferential groove 1418 as the locking member was rotated from the first position to the second position.

Figure 14A:
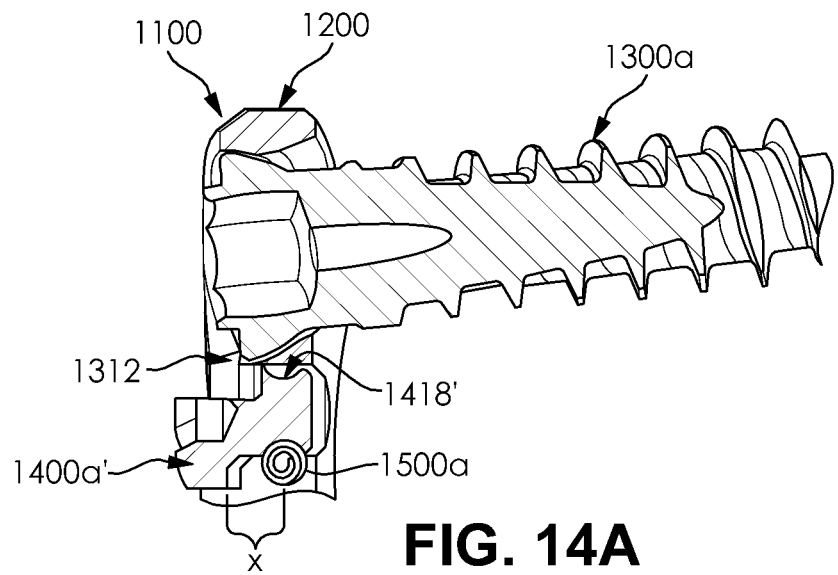
FIG. 14A is a magnified partial sectional view of the osteosynthesis system illustrated in FIG. 11. The locking member is shown in a first configuration.
Figure 14B:
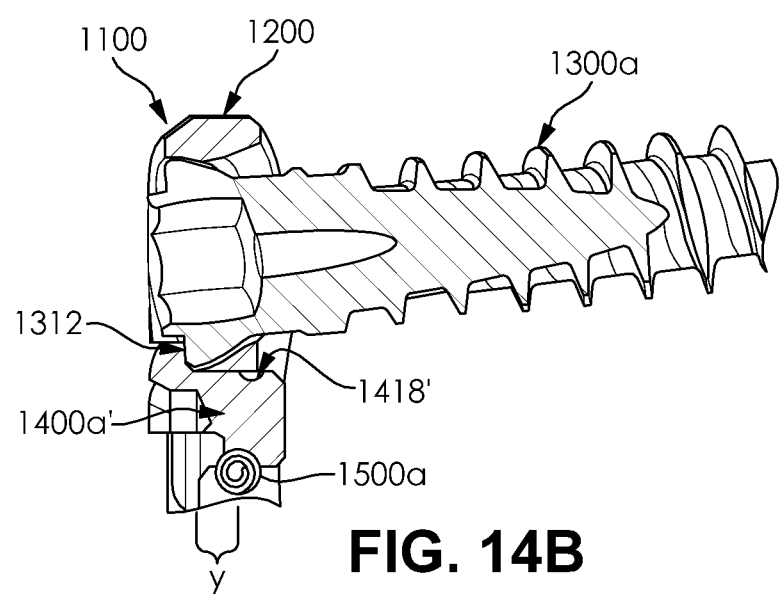
FIG. 14B is a magnified partial sectional view of the osteosynthesis system illustrated in FIG. 11. The locking member is shown in a second configuration.

Each of FIGS. 14A and 14B illustrates a portion of the osteosynthesis system 1100 that includes an alternative locking member 1400a' in which the circumferential groove 1418' is disposed at a substantially opposite angle than that in the embodiment illustrated in FIGS. 13A and 13B. A plate 1200 and an anchor 1300a having a circumferential shoulder 1312 are also illustrated in FIGS. 14A and 14B. As a result of this configuration, the distance x is greater than the distance y, such that the locking member 1400a' has telescoped in an inwardly direction as a result of the pin 1500a traveling through the circumferential groove 1418' as the locking member 1400a' was rotated from the first position to the second position.

A plate in an osteosynthesis system according to a particular embodiment can include various structural adaptations to make the plate and osteosynthesis system better suite for a particular application while still retaining required structure. For example, FIGS. 15 and 16 illustrate another osteosynthesis system 2100 or one or more components thereof. The illustrated osteosynthesis system 2100 is similar to the osteosynthesis system 100 described above, except as described below. Thus, osteosynthesis system 2100 includes a plate 2200, a set of anchors (not illustrated in FIGS. 15 and 16), a set of locking members 2400a, 2400b, 2400c, 2400d, and a set of pins 2500a, 2500b, 2500c, 2500d. The plate 2200 defines three sets of passageways: anchor passageways 2216, 2218, 2220, 2222; locking member passageways 2232, 2234, 2236, 2238; and pin passageways 2250, 2252, 2254, 2256. Each of the locking member passageways 2232, 2234, 2236, 2238 partially intersects one of the anchor passageways 2216, 2218, 2220, 2222. Each of the pin passageways 2250, 2252, 2254, 2256 provides a passageway extending from the side 2240 of the main body 2202 of the plate 2200 to one of the locking member passageways 2232, 2234, 2236, 2238. Each of the anchors (not illustrated in FIGS. 15 and 16) is disposed in one of the anchor passageways 2216, 2218, 2220, 2222. Each of the locking members 2400a, 2400b, 2400c, 2400d is disposed in one of the locking member passageways 2232, 2234, 2236, 2238 and is rotatable within the respective one of the locking member passageways 2232, 2234, 2236, 2238. Each of the pins 2500*a*, 2500*b*, 2500*c*, 2500*d* is disposed in one of the pin passageways 2250, 2252, 2254, 2256.

In this embodiment, plate 2200 defines an additional pair of anchor passageways 2223, 2225, an additional pair of locking member passageways 2239, 2241, and an additional pair of pin passageways 2257, 2259. Accordingly, the plate assembly includes an additional pair of locking members 2400*e*, 2400*f*, an additional pair of pins 2500*e*, 2500*f*, and an additional pair of anchors (not illustrated in FIGS. 15 and 16). Inclusion of additional passageways in this manner allows the plate to be attached to additional vertebrae, for example, extending the length and number of vertebrae across which the osteosynthesis system is useful. If additional passageways are included in a plate of an osteosynthesis system according to a particular embodiment, any suitable number of additional passageways, and the respective components that are disposed in the passageways, can be included. It is considered advantageous to add sets of additional passageways in pairs of each type of passageways. Thus, while any number of additional passageways can be included, inclusion of 2 additional passageways of each type (6 total passageways of each type), 4 additional passageways of each type (8 total passageways of each type), 6 additional passageways of each type (10 total passageways of each type), or 8 additional passageways of each type (12 total passageways of each type) in a plate of an osteosynthesis system according to a particular embodiment is considered suitable.

Figure 16A:
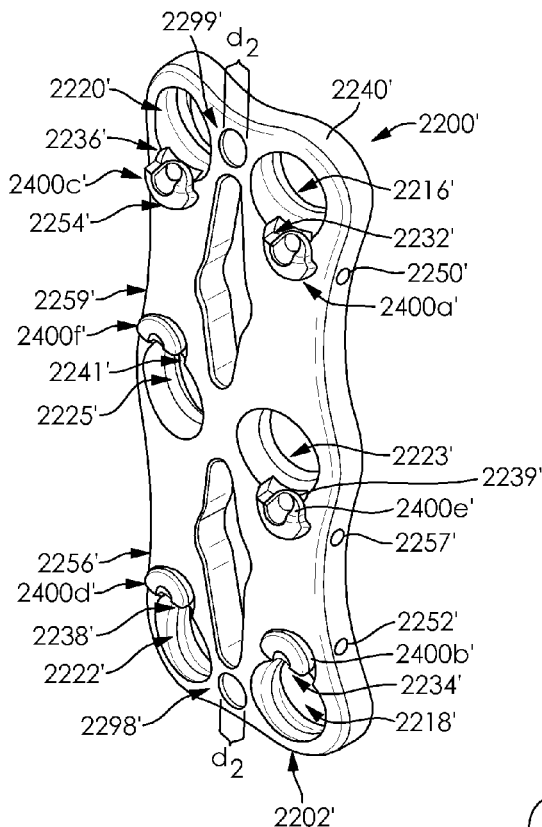
FIG. 16A is a perspective view of an alternative plate and six locking members.

FIG. 16A illustrates components of another osteosynthesis system. FIG. 16A illustrates an alternative plate 2200' having a main body 2202' and locking members 2400*a'*, 2400*b'*, 2400*c'*, 2400*d'*, 2400*e'*, 2400*f'*. The alternative osteosynthesis system is similar to the osteosynthesis system 2100 described above, except as described below. Thus, the alternative osteosynthesis system includes a plate 2200', a set of anchors (not illustrated in FIG. 16A), a set of locking members 2400*a'*, 2400*b'*, 2400*c'*, 2400*d'*, 2400*e'*, 2400*f'* and a set of pins (not illustrated in FIG. 16A).

The plate 2200' defines three sets of passageways: anchor passageways 2216' 2218', 2220', 2222', 2223', 2225'; locking member passageways 2232', 2234', 2236', 2238', 2239', 2241'; and pin passageways 2250', 2252', 2254', 2256', 2257', 2259'. Each of the locking member passageways 2232', 2234', 2236', 2238', 2239', 2241' partially intersects one of the anchor passageways 2216' 2218', 2220', 2222', 2223', 2225'. Each of the pin passageways 2250', 2252', 2254', 2256', 2257', 2259' provides a passageway extending from the side 2240' of the main body 2202' of the plate 2200' to one of the locking member passageways 2232', 2234', 2236', 2238', 2239', 2241'. Each of the anchors is disposed in one of the anchor passageways 2216' 2218', 2220', 2222', 2223', 2225'. Each of the locking members 2400*a'*, 2400*b'*, 2400*c'*, 2400*d'*, 2400*e'*, 2400*f'* is disposed in one of the locking member passageways 2232', 2234', 2236', 2238', 2239', 2241' and is rotatable within the respective one of the locking member passageways 2232', 2234', 2236', 2238', 2239', 2241'. Each of the pins is disposed in one of the pin passageways 2250', 2252', 2254', 2256', 2257', 2259'. The plate 2200' also defines a lower cavity 2298' and an upper cavity 2299'. The lower and upper cavities 2298', 2299' each define a diameter $d_2$.

In this embodiment, the lower cavity 2298' is disposed between two anchor passageways 2218', 2222', while the upper cavity 2299' is disposed between two other anchor passageways 2216', 2220'. The lower and upper cavities 2298', 2299' assist in alignment of the plate 2200' prior to the placement of the anchors. Each of the lower and upper cavities 2298', 2299' has a circular cross-sectional shape; furthermore, the lower and upper cavities 2298', 2299' have equal diameters $d_2$. In other embodiments, each of the lower cavity and the upper cavity may be disposed at any other location on the plate. In a different embodiment, the plate may only define an upper cavity. The lower and upper cavities may also have any cross-sectional shape, including triangular, square, rectangular, elliptical, pentagonal, or any other shape. Additionally, the lower cavity may have a diameter that is greater than or less than the diameter of the upper cavity. A skilled artisan will be able to determine a suitable placement of, diameter of, and cross-sectional shape of each of the lower and upper cavities based on a variety of factors, including the size of the plate, the size of the locking members, and the size of the anchors.

Figure 17:
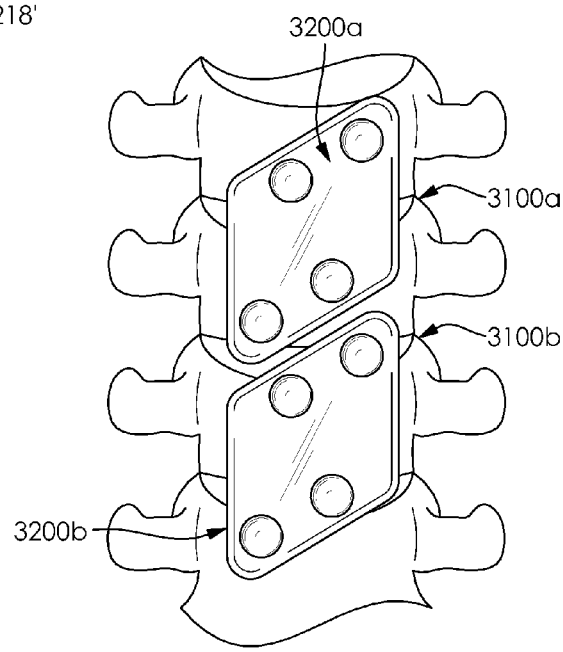
FIG. 17 is a partial top view of the cervical region of a patient into which two osteosynthesis systems have been implanted in a stacking relationship.

Also, the plate in an osteosynthesis system according to a particular embodiment can have any suitable shape and the shapes included in the embodiments described above are exemplary in nature. Examples of other suitable shapes include, but are not limited to, circular, rhomboidal and trapezoidal plates. A skilled artisan will be able to select an appropriate shape for a plate in an osteosynthesis system according to a particular embodiment based on various considerations, including the intended location at which the system is to be installed, and whether additional systems will be or may be installed at an adjacent location in a patient. For example, FIG. 17 illustrates two osteosynthesis systems 3100*a*, 3100*b* installed in a stacking arrangement in adjacent cervical locations within a patient. The plate 3200*a*, 3200*b* of each osteosynthesis system has a rhomboidal shape that facilitates this stacking placement.

The locking members in an osteosynthesis system according to a particular embodiment can be configured to engage more than one anchor and lock each of the more than one anchors in the anchor passageway within which the respective each of the more than one anchors is disposed. For example, a locking member can be configured to engage and lock two, three or more anchors when rotated.

Figure 18:
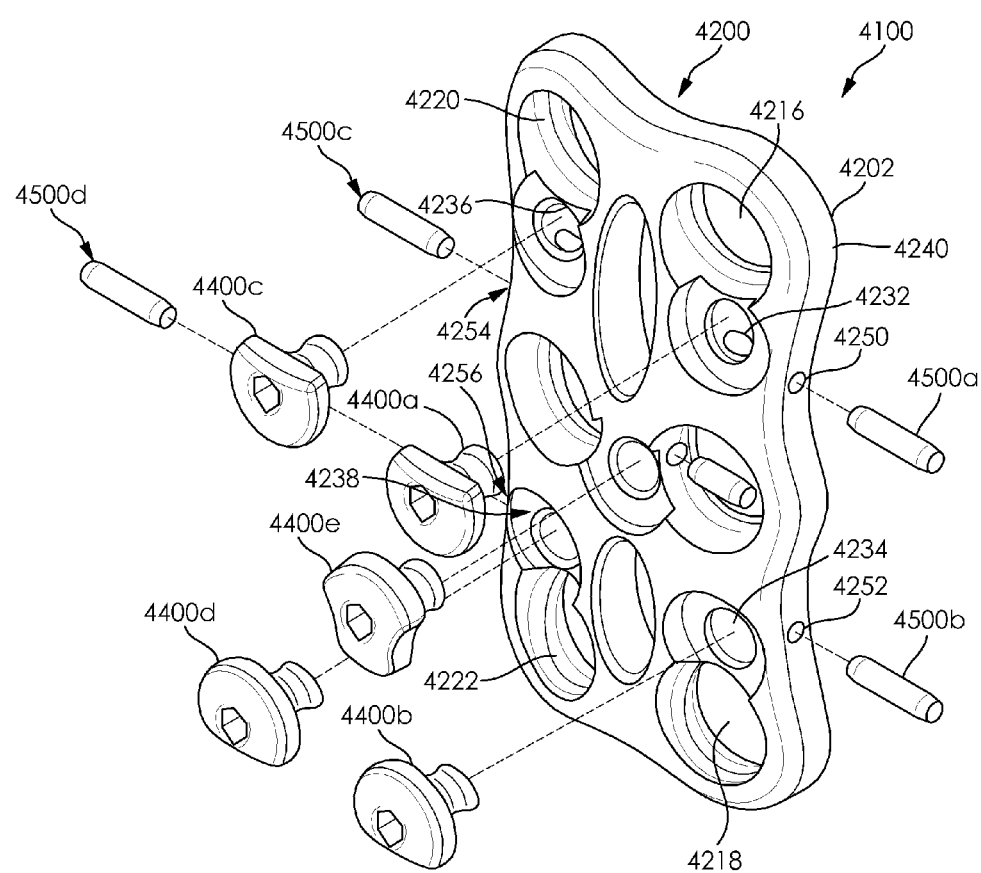
FIG. 18 is an exploded view of another osteosynthesis system.

For example, FIG. 18 illustrates an osteosynthesis system 4100 that includes two different types of locking members. The illustrated osteosynthesis system 4100 is similar to the osteosynthesis system 100 described above, except as described below. Thus, osteosynthesis system 4100 includes a plate 4200, a set of anchors (not illustrated in FIG. 18), a set of locking members 4400*a*, 4400*b*, 4400*c*, 4400*d*, and a set of pins 4500*a*, 4500*b*, 4500*c*, 4500*d*. The plate 4200 defines three sets of passageways: anchor passageways 4216, 4218, 4220, 4222; locking member passageways 4232, 4234, 4236, 4238; and pin passageways 4250, 4252, 4254, 4256. Each of the locking member passageways 4232, 4234, 4236, 4238 partially intersects one of the anchor passageways 4216, 4218, 4220, 4222. Each of the pin passageways 4250, 4252, 4254, 4256 provides a passageway extending from the side 4240 of the main body 4202 of the plate 4200 to one of the locking member passageways 4232, 4234, 4236, 4238. Each of the anchors (not illustrated in FIG. 18) is disposed in one of the anchor passageways 4216, 4218, 4220, 4222. Each of the locking members 4400*a*, 4400*b*, 4400*c*, 4400*d* is disposed in one of the locking member passageways 4232, 4234, 4236, 4238 and is rotatable within the respective one of the locking member passageways 4232, 4234, 4236, 4238. Each of the pins 4500*a*, 4500*b*, 4500*c*, 4500*d* is disposed in one of the pin passageways 4250, 4252, 4254, 4256.

In this embodiment, each of the locking members located at the proximal and distal ends of the plate is configured to engage and lock a single anchor when rotated within its respective locking member passageway. In contrast, a locking member disposed between the proximal and distal ends of the plate, in a locking member passageway, is configured to lock and secure two anchors when rotated within its locking member passageway. In this embodiment, each of the anchor passageways that interfaces with the locking member passageway disposed between the proximal and distal ends of the plate is adapted to position the anchor at a perpendicular or substantially perpendicular angle relative to the top surface of the plate where it defines each of these anchor passageways. In this manner, the osteosynthesis system of this embodiment is adapted to provide a desired hyperangulation at the proximal and distal ends of the plates, while providing a desired simplified locking procedure in the middle of the plate.

The osteosynthesis systems are useful in a variety of orthopedic procedures. Particular embodiments, including the specific embodiments illustrated and described in detail herein, are useful in a variety of cervical related orthopedic procedures, including Anterior Cervical Surgery (ACS) and Anterior Cervical Discectomy and Fusion (ACDF) procedures. An ACS procedure can involve augmentation of the vertebral body and/or uncinate process from an anterior approach. An ACDF procedure can involve performing a decompression of the nerve roots through a discectomy anteriorly and performing an interbody fusion to avoid radiculopathy from foraminal narrowing and the possibility of developing late kyphosis from disc space collapse. Fusion can be achieved by placement of plates and screws, such as those provided by an osteosynthesis system according to an embodiment, and with or without a graft.

As described herein, a plate assembly includes the plate, locking members, and pins of an osteosynthesis system. A plate assembly does not include the anchors of an osteosynthesis system.

All components of the osteosynthesis systems, plate assemblies and anchors can be made from any suitable material. Non-limiting examples of suitable materials include metals, such as stainless steel, titanium, cobalt-chromium, and other metals, and plastics commonly used in medical devices. Non-limiting examples of materials considered specifically suitable for use in the compression member and retaining member include Nitinol and other superelastic materials, polyurethane materials, silicone materials, and polyether ether ketone (PEEK) materials.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

We claim:

1. An osteosynthesis system, comprising:
a plate having a main body having a longitudinal axis, first and second opposing sides, and first and second opposing ends, and defining a set of anchor passageways, a set of locking member passageways, and a set of pin passageways, each of the locking member passageways partially intersecting one of the anchor passageways and each of the pin passageways providing a passageway extending from one of the first and second opposing sides of the main body to one of the locking member passageways;
a set of anchors, each anchor disposed in one of the anchor passageways and defining a proximal surface, a distal end, and a circumferential shoulder located distal to the proximal surface;
a set of locking members, each locking member defining a circumferential groove, each locking member disposed in one of the locking member passageways, and each locking member rotatable within the one of the locking member passageways to engage the circumferential shoulder of the anchor disposed in the anchor passageway partially intersected by the one of the locking member passageways; and
a set of pins, each pin disposed in one of the pin passageways and partially disposed within the circumferential groove defined by the locking member disposed in the locking member passageway in communication with the pin passageway.

2. The osteosynthesis system of claim 1, wherein each of the locking members is configured to engage only a single anchor.

3. The osteosynthesis system of claim 1, wherein one of the locking members is configured to engage two anchors.

4. The osteosynthesis system of claim 1, wherein each locking member of a first subset of the set of locking members is configured to secure and lock only a single anchor and each locking member of a second subset of the set of locking members is configured to engage more than one anchor.

5. The osteosynthesis system of claim 1, wherein the set of anchor passageways includes first and second anchor passageways at a first end of the plate and third and fourth anchor passageways at a second, opposite end of the plate.

6. The osteosynthesis system of claim 5, wherein the set of locking member passageways includes first and second locking member passageways disposed at the first end of the plate.

7. The osteosynthesis system of claim 6, wherein the first locking member passageway intersects the first anchor passageway.

8. The osteosynthesis system of claim 7, wherein the locking member disposed in the first locking member passageway is configured to engage only the first anchor disposed in the first anchor passageway.

9. The osteosynthesis system of claim 8, wherein the second locking member passageway intersects the second anchor passageway.

10. The osteosynthesis system of claim 9, wherein the locking member disposed in the second locking member passageway is configured to engage only the second anchor disposed in the second anchor passageway.

11. The osteosynthesis system of claim 10, wherein the set of locking member passageways includes third and fourth locking member passageways disposed at the second end of the plate.

12. The osteosynthesis system of claim 11, wherein the third locking member passageway intersects the third anchor passageway.

13. The osteosynthesis system of claim 12, wherein the locking member disposed in the third locking member passageway is configured to engage only the third anchor disposed in the third anchor passageway.

14. The osteosynthesis system of claim 13, wherein the fourth locking member passageway intersects the fourth anchor passageway.

15. The osteosynthesis system of claim 14, wherein the locking member disposed in the fourth locking member passageway is configured to engage only the fourth anchor disposed in the fourth anchor passageway.

16. The osteosynthesis system of claim 15, wherein the set of anchor passageways includes a first lateral anchor passageway and a second lateral anchor passageway disposed between the anchor passageways disposed on the first and second ends of the plate.

17. The osteosynthesis system of claim 16, wherein the set of locking member passageways includes a central locking member passageway that partially intersects the first and second lateral anchor passageways; and wherein the locking member disposed in the central locking member passageway is configured to engage both a first lateral anchor disposed in the first lateral anchor passageway and a second lateral anchor disposed in the second lateral anchor passageway.

18. An osteosynthesis system comprising a plate defining a main body having a longitudinal axis, first and second opposing sides, and first and second opposing ends, a first series of anchor passageways, a second series of anchor passageways, a set of anchors, each anchor of the set of anchors individually disposable within an anchor passageway of the first and second series of anchor passageways, and a set of locking members, each locking member of the set of locking members defining a circumferential groove and configured to engage at least one anchor of the set of anchors to retain the at least one anchor within an anchor passageway of one of the first and second series of anchor passageways;

wherein each anchor passageway of the first series of anchor passageways allows an anchor of the set of anchors to be disposed at a hyperangulation angle; and wherein each anchor passageway of the second series of anchor passageways does not allow an anchor of the set of anchors to be disposed at a hyperangulation angle;

wherein the plate defines a series of pin passageways, each pin passageway of the series of pin passageways providing a passageway extending from one of the first and second opposing sides of the main body to one of the locking member passageways; and a set of pins, each pin disposed in one of the pin passageways and partially disposed within the circumferential groove defined by the locking member disposed in the locking member passageway in communication with the pin passageway.

* * * * *